US008071295B2

(12) United States Patent
Ashby

(10) Patent No.: US 8,071,295 B2
(45) Date of Patent: Dec. 6, 2011

(54) DNA-BASED METHODS OF GEOCHEMICAL PROSPECTING

(76) Inventor: Matthew Ashby, Mill Valley, CA (US)

(*) Notice: Subject to any disclaimer, the term of this patent is extended or adjusted under 35 U.S.C. 154(b) by 512 days.

(21) Appl. No.: 10/607,077

(22) Filed: Jun. 25, 2003

(65) Prior Publication Data

US 2004/0110183 A1    Jun. 10, 2004

Related U.S. Application Data

(62) Division of application No. 09/829,855, filed on Apr. 10, 2001, now Pat. No. 6,613,520.

(60) Provisional application No. 60/196,063, filed on Apr. 10, 2000, provisional application No. 60/196,258, filed on Apr. 11, 2000.

(51) Int. Cl.
*C12Q 1/68* (2006.01)
*C12P 19/34* (2006.01)
*C07H 21/02* (2006.01)
*C07H 21/04* (2006.01)

(52) U.S. Cl. .................. 435/6.1; 435/91.2; 536/23.1
(58) Field of Classification Search ................. None
See application file for complete search history.

(56) References Cited

U.S. PATENT DOCUMENTS

| 5,055,397 A | 10/1991 | Michaels et al. | 435/9 |
| 5,093,236 A | 3/1992 | Gonzalez-Prevatt et al. | 435/9 |
| 5,695,937 A | 12/1997 | Kinzler et al. | 435/6 |
| 5,866,330 A | 2/1999 | Kinzler et al. | 435/6 |
| 5,981,190 A | 11/1999 | Israel | 435/6 |
| 6,613,520 B2 | 9/2003 | Ashby | 435/6 |

OTHER PUBLICATIONS

Telang, A.J. et al., "Characterization of the diversity of sulfate-reducing bacteria in soil and mining waste water environments by nucleic acid hybridization techniques", Can. J. Microbiol., vol. 40, pp. 955-964 (1994).*
Golsteyn Thomas, E.J. et al., Appl. Env. Microbiol., vol. 57, pp. 2576-2580 (1991).*
Leu, J.-Y. et al., Anaerobe, vol. 4, pp. 165-174 (1998).*
Colbert, S. F. et al., Appl. Environ. Microbiol., vol. 59, pp. 2056-2063 (1996).*
Wikstrom, P. et al., J. Biotechnol., vol. 52, pp. 107-120 (1996).*
Clarke, S.D. et al., J. Nutr., vol. 120, pp. 218-224 (1990).*
Matsuki, T. et al., Appl. Environ. Microbiol., vol. 65, pp. 4506-4512 (Oct. 1999).*
Devereux, R. et al., Appl. Env. Microbiol., vol. 60, pp. 3437-3439 (1994).*
Farrelly, Vincent et al., "Effect of Genome Size and *rrn* Gene Copy Number on PCR Amplification of 16S rRNA Genes from a Mixture of Bacterial Species," *Applid and Environmental Microbiology* 61(7): 2798-2801 (1995).

Hugenholtz, Philip et al., "Impact of Culture-Independent Studies on the Emerging Phylogenetic View of Bacterial Diversity," *Journal of Bacteriology* 180(18): 4765-4774 (1998).
Liu, Wen-Tso et al., "Characterization of Microbial Diversity by Determining Terminal Restriction Fragment Length Polymorphisms of Genes Encoding 16S rRNA," *Applied and Environmental Microbiology* 63(11): 4516-4522 (1997).
Margulies, Elliot H. et al., "eSAGE: Managing and Analysing Data Generated with Serial Analysis of Gene Expression (SAGE)," *Bioinformatics* 16(7): 650-651 (2000).
Muyzer, Gerard et al., "Profiling of Complex Microbial Populations by Denaturing Gradient Gel Electrophoresis Analysis of Polymerase Chain Reaction-Amplified Genes Coding for 16S rRNA," *Applied and Environmental Microbiology* 59(3): 695-700 (1993).
Pace, Norman R., "A Molecular View of Microbial Diversity and the Biosphere," *Science* 276: 734-740 (1997).
Reiman, David A., "Detection and Identification of Previously Unrecognized Microbial Pathogens," *Emerging Infectious Diseases* 4(3): 382-389 (1998).
Torsvik, Vigdis et al., "High Diversity in DNA of Soil Bacteria," *Applied and Environmental Microbiology* 56(3): 782-787 (1990).
Unrau, Paul et al., "Non-cloning Amplification of Specific DNA Fragments from Whole Genomic DNA digests using DNA 'Indexers'," *Gene* 145: 163-169 (1994).
Velculescu, Victor E. et al., "Serial Analysis of Gene Expression," *Science* 270: 484-487 (1995).
Voordouw, Gerrit et al., "Characterization of 16S rRNA Genes from Oil Field Microbial Communities Indicates the Presence of a Variety of Sulfate-Reducing, Fermentative, and Sulfide-Oxidizing Bacteria," *Applied and Environmental Microbiology* 62(5): 1623-1629 (1996).
Zhang, Lin et al., "Gene Expression Profiles in Normal and Cancer Cells," *Science* 276: 1268-1272 (1997).
Felske et al. "Phylogeny of the main bacterial 16S rRNA sequences in drentse a grassland soils (The Netherland)," *Applied and Environmental Microbiology*, 64:871-879 (1998).
Wang et al., "Frequency of formation of chimeric molecules as a consequence of PCR coamplification of 16S rRNA genes from mixed bacterial genomes," *Applied and Environmental Microbiology*, 63: 4645-4650 (1997).
Wintzingerode et al., "Determination of microbial diversity in environmental samples: pitfalls of PCR-based rRNA analysis," *FEMS Microbiology Reviews*, 21: 213-229 (1997).
Larsen et al., "The ribosomal database project," *Nucleic Acids Research*, 21:3021-3023 (1993).

* cited by examiner

*Primary Examiner* — Teresa E Strzelecka
(74) *Attorney, Agent, or Firm* — Ropes & Gray LLP; James F. Haley, Jr.; Yang Xu

(57) ABSTRACT

The present invention relates to methods for performing surveys of the genetic diversity of a population. The invention also relates to methods for performing genetic analyses of a population. The invention further relates to methods for the creation of databases comprising the survey information and the databases created by these methods. The invention also relates to methods for analyzing the information to correlate the presence of nucleic acid markers with desired parameters in a sample. These methods have application in the fields of geochemical exploration, agriculture, bioremediation, environmental analysis, clinical microbiology, forensic science and medicine.

17 Claims, 18 Drawing Sheets

**Bacteria
16s rRNA Polymorphic Regions**

Bacteria

Acidobacteria Group
    Various uncultured environmental Acidobacteria
Aquificales
  Desulfurobacterium Group
    Desulfurobacterium
      *Desulfurobacterium thermolithotrophum*
    environmental samples
      unidentified Aquificales OPS132
CFB/Green sulfur bacteria group
  Bacteroidaceae
    Bacteroides
      *Bacteroides caccae*
Firmicutes(gram-positive bacteria)
  Actinobacteria(high G+C gram-positive bacteria)
    Actinomycetaceae
      Actinomyces
        *Actinomyces bovis*
        *Actinomyces meyeri*
      Denitrobacterium
        *Denitrobacterium detoxificans*
Green non-sulfur bacteria
    environmental samples
      uncultured HC-seep bacterium BPC110
      uncultured HC-seep bacterium GCA004
      uncultured HC-seep bacterium GCA112
Proteobacteria(purple non-sulfur bacteria)
  alpha subdivision
    Acetobacteraceae
      Acetobacter
        *Acetobacter aceti*
      Gluconobacter
        *Gluconobacter asaii*
  beta subdivision
    Burkholderia group
      Burkholderia
        *Burkholderia* sp. JB1
      Denitrobacter
        *Denitrobacter permanens*
  delta subdivision
    Desulfobacter
      *Desulfobacter curvatus*
    Desulfobulbus
      *Desulfobulbus* sp. BG25
    Legionellaceae
      Legionella
        *Legionella anisa*
unclassified Bacteria
      benzene mineralizing clone SB-1
      uncultured eubacterium env.OPS 1

FIG. 3

Archaea (archaebacteria)
Crenarchaeota (extremely thermophilic archaebacteria)
   Desulfurococcales
      Desulfurococcaceae
         Aeropyrum
            *Aeropyrum pernix*
         Desulfurococcus
            *Desulfurococcus mobilis*
         Staphylothermus
            *Staphylothermus marinus*
   Sulfolobales
      Metallosphaera
         *Metallosphaera sedula*
      Sulfolobus
         *Sulfolobus acidocaldarius*
         *Sulfolobus metallicus*
   Thermoproteales
      Thermoproteaceae
         Caldivirga
            *Caldivirga maquilingensis*
      Pyrobaculum
         *Pyrobaculum islandicum*
Euryarchaeota
   Archaeoglobales
      Archaeoglobaceae
         Archaeoglobus
            *Archaeoglobus fulgidus*
            *Archaeoglobus veneficus*
   Halobacteriales
      Halobacteriaceae
         Haloarcula
            *Haloarcula japonica*
         Halococcus
            *Halococcus morrhuae*
   Methanococcales
      Methanococcaceae
         Methanococcus
            *Methanococcus jannaschii*
   Methanobacteriales
      Methanobacteriaceae
         Methanobacterium
            *Methanobacterium bryantii*
            *Methanobacterium subterraneum*
   Thermococcales
      Thermococcaceae
         Pyrococcus
            *Pyrococcus abyssi*
   Thermoplasmales
      Picrophilaceae
         Picrophilus
            *Picrophilus oshimae*

FIG. 4

SARD OLIGONUCLEOTIDES

```
TX-003    5'-  Phosphate-GCTCCAGGTCTACATCCTAGTCAGGACddC-3'
TX-012    5'-  Phosphate- CTCCAGGTCTACATCCTAGTCAGGACddC
TX-010R   3'              GAGGTCCAGATGTAGGATCAGTCCTGGATA-5'
TX-013    3'              GAGGTCCAGATGTAGGATCAGTCCTGGATA-5'
TX-004R   3'                    CAGATGTAGGATCAGTCCTGGATA-5'
TX-007R   3'-                   CAGATGTAGGATCAGTCCTGG -Biotin-5'
TX-111    3'-                   CAGATGTAGGATCAGTCCTGGCACTGATAGCTC -Biotin-5'

TX-005    5'-  Phosphate-GCTCCAGACTAGCATCCGCTGACTTGAddC
TX-014    5'-  Phosphate- CTCCAGACTAGCATCCGCTGACTTGAddC
TX-011R   3'              GAGGTCTGATCGTAGGCGACTGAACTGTAA
TX-015    3'              GAGGTCTGATCGTAGGCGACTGAACTGTAA
TX-006R   3'                    TGATCGTAGGCGACTGAACTGTAA
TX-008R   3'                    TGATCGTAGGCGACTGAACTG -Biotin-5'
TX-121    3'                    TGATCGTAGGCGACTGAACTGGCAACGTTGGAC -Biotin-5'
```

TX-001    5'- Biotin-GTG TAG HRG TGA AAT DCD YA (SEQ ID NO:138)

TX-002    5'- YTC ACG RCA YGA GCT GAC GAC (SEQ ID NO:139)

TX-003    5'- Phosphate-GCT CCA GGT CTA CAT CCT AGT CAG GACddC (SEQ ID NO:140)

TX-004    5'- ATA GGT CCT GAC TAG GAT GTA GAC (SEQ ID NO:141)

TX-005    5'- Phosphate-GCT CCA GAC TAG CAT CCG CTG ACT TGAddC (SEQ ID NO:142)

TX-006    5'- AAT GTC AAG TCA GCG GAT GCT AGT (SEQ ID NO:143)

TX-007    5'- Biotin-GGT CCT GAC TAG GAT GTA GAC (SEQ ID NO:144)

TX-008    5'- Biotin-GTC AAG TCA GCG GAT GCT AGT (SEQ ID NO:145)

TX-009    5'- Biotin-GGA TTA GAW ACC CBG GTA GTC (SEQ ID NO:146)

TX-010    5'- ATA GGT CCT GAC TAG GAT GTA GAC CTG GAG (SEQ ID NO:147)

TX-011    5'  AAT GTC AAG TCA GCG GAT GCT AGT CTG GAG (SEQ ID NO:148)

TX-012    5'- Phosphate-CTC CAG GTC TAC ATC CTA GTC AGG AcddC (SEQ ID NO:149)

TX-013    5'- ATA GGT CCT GAC TAG GAT GTA GAC CTG GAG (SEQ ID NO:150)

TX-014    5'- Phosphate-CTC CAG ACT AGC ATC CGC TGA CTT GaddC (SEQ ID NO:151)

TX-015    5'  AAT GTC AAG TCA GCG GAT GCT AGT CTG GAG (SEQ ID NO:152)

TX-111    5'  Biotin-CTC GAT AGT CAC GGT CCT GAC TAG GAT GTA GAC (SEQ ID NO:153)

TX-121    5'  Biotin-CAG GTT GCA ACG GTC AAG TCA GCG GAT GCT AGT (SEQ ID NO:154)

FIG. 12

SARD STRATEGY

1. Amplify rDNA with TX-009 and 1392R

```
Bio------nnnnNNNNNNNNNNNNAGCTnnnnnnnnnnnnnnn
        nnnnNNNNNNNNNNNNTCGAnnnnnnnnnnnnnnn
```

2. Cut with AluI.

```
Bio------nnnnNNNNNNNNNNAG         CTnnnnnnnnnnnnnnn
        nnnnNNNNNNNNNNNNTC        GAnnnnnnnnnnnnnnn
```

3. Split into two pools, bind to SA beads, wash, add TX-12/13 adapter or TX-14/15 adapter.

```
Bio------nnnnNNNNNNNNNNNAG    CTCCAGGTCTACATCCTAGTCAGGACddC -3'  (TX012)
        nnnnNNNNNNNNNNNNNTC   GAGGTCCAGATGTAGGATCAGTCCTGATA-5'   (TX013)
```

OR

```
Bio------nnnnNNNNNNNNNNNAG    CTCCAGACTAGCATCCGCTGACTTGAddC -3'  (TX014)
        nnnnNNNNNNNNNNNNNTC   GAGGTCTGATCGTAGGCGACTGAACTGTAA-5'  (TX015)
```

4. Ligate adapters, wash.

```
Bio------nnnnNNNNNNNNNNNAGCTCCAGGTCTACATCCTAGTCAGGACddC -3'  (TX012)
        nnnnNNNNNNNNNNNNNTCGAGGTCCAGATGTAGGATCAGTCCTGATA-5'   (TX013)
```

FIG. 13

5. Cleave with Bpml, remove SA-beads.

NNNNNNNNNNNAGCTCCAGGTCTACATCCTAGTCAGGACddC -3' (TX012)
nnNNNNNNNNNNTCGAGGTCCAGATGTAGGATCAGTCCTGATA-5' (TX013)

6. Remove 3' termini with PolI plus 4 dNTPs, combine pools, ligate.

(TX015)                                                                                                    (TX012)
AATGTCAAGTCAGCGGATGCTAGTCTGGAGCTNNNNNNNNNNNNNNNNNNNNNAGCTCCAGGTCTACATCCTAGTCAGGACddC -3'
ddCAGTTCAGTCGCCTACGATCAGACCTCGAANNNNNNNNNNNNNNNNNNNNNTCGAGGTCCAGATGTAGGATCAGTCCTGATA-5'
                                                                                                           (TX013)
(TX014)

7. Amplify ditags with TX-111, TX-121 primers

BioCAGGTTGCAACGGTCAAGTCAGCGGATGCTAGT---------->
    AATGTCAAGTCAGCGGATGCTAGTCTGGAGCTNNNNNNNNNNNNNNNNNNNNNAGCTCCAGGTCTACATCCTAGTCAGGACddC -3
    ddCAGTTCAGTCGCCTACGATCAGACCTCGAANNNNNNNNNNNNNNNNNNNNNTCGAGGTCCAGATGTAGGATCAGTCCTGATA-5'
                                              <-----CAGATGTAGGATCAGTCCTGGCACTGATAGCTC-Bio

8. Purify PCR product, cleave with AluI

BioCAGGTTGCAACGGTCAAGTCAGCGGATGCTAGTCTGGAG    CTNNNNNNNNNNNNNNNNNNNNNAGCTCCAGGTCTACATCCTAGTCAGGACCGTGACTATCGAG-3'
GTCCAACGTTGCCAGTTCAGTCGCCTACGATCAGACCTC    GANNNNNNNNNNNNNNNNNNNNNTCGAGGTCCAGATGTAGGATCAGTCCTGGCACTGATAGCTC-Bio

9. Purify away adapters, ligate.

CTNNNNNNNNNNNNNNNNNNNNNAGCTNNNNNNNNNNNNNNNNNNNNNAGCTNNNNNNNNNNNNNNNNNNNNNAG
GANNNNNNNNNNNNNNNNNNNNNTCGANNNNNNNNNNNNNNNNNNNNNTCGANNNNNNNNNNNNNNNNNNNNNTC

10. G l-purify large concatemers, clone into SmaI site of vector.

FIG. 13 (cont.)

ACGATGAGCACTAGCT
(SEQ ID NO:1) (1)

ACGATGAGTACTAGCT
(SEQ ID NO:2) (1)

ACGATGATGACTAGCT
(SEQ ID NO:3) (2)

ACGATGGATGCTAGCT
(SEQ ID NO:4) (1)

ATGCTAGTCTGGAGCT
(SEQ ID NO:5) (6)

ATGGCTGTCGTCAGCT
(SEQ ID NO:6) (50)

ATGGTTGTCGTCAGCT
(SEQ ID NO:7) (1)

ATTCCGTGCCGTAGCT
(SEQ ID NO:8) (1)

CACTAGTGGCGCAGCT
(SEQ ID NO:9) (2)

CCCCCGTGCCGAAGCT
(SEQ ID NO:10) (1)

CCCCCGTGCCGCAGCT
(SEQ ID NO:11) (1)

CCCCCTTCCTCCAGCT
(SEQ ID NO:12) (1)

CCCCGGTGCCGCAGCT
(SEQ ID NO:13) (1)

CCGGGTAGTCCCAGCT
(SEQ ID NO:14) (5)

CCTCCGTGCCGAAGCT
(SEQ ID NO:15) (3)

CCTCCGTGCCGCAGCT
(SEQ ID NO:16) (2)

CCTCCGTGCTGCAGCT
(SEQ ID NO:17) (1)

CCTCGGCGCCGCAGCT
(SEQ ID NO:18) (2)

CCTCGGTGCCGCAGCT
(SEQ ID NO:19) (1)

CCTCGGTGTCGCAGCT
(SEQ ID NO:20) (2)

CCTGGGTGCCGCAGCT
(SEQ ID NO:21) (2)

CCTGTGTGACGAAGCT
(SEQ ID NO:22) (1)

CCTTGGTAACGAAGCT
(SEQ ID NO:23) (1)

CCTTGGTACCGAAGCT
(SEQ ID NO:24) (1)

CGCCAGTGCCGTAGCT
(SEQ ID NO:25) (1)

CGCCTGTGCCGTAGCT
(SEQ ID NO:26) (2)

CGTCCGTGCCGAAGCT
(SEQ ID NO:27) (2)

CGTCCGTGCCGCAGCT
(SEQ ID NO:28) (1)

CGTCGGTGCCGCAGCT
(SEQ ID NO:29) (3)

CTCCCGTGCCGCAGCT
(SEQ ID NO:30) (1)

CTCCCGTGCCGGAGCT
(SEQ ID NO:31) (1)

CTCCGGTGCCGCAGCT
(SEQ ID NO:32) (1)

CTCCTGTGCCGAAGCT
(SEQ ID NO:33) (1)

CTCCTGTGCCGCAGCT
(SEQ ID NO:34) (2)

CTGCCGTGCCGAAGCT
(SEQ ID NO:35) (9)

CTGCTGTGCCGAAGCT
(SEQ ID NO:36) (2)

CTGTCGTGCCGAAGCT
(SEQ ID NO:37) (1)

CTTCAGTATCGAAGCT
(SEQ ID NO:38) (1)

CTTCCGCGCCGGAGCT
(SEQ ID NO:39) (2)

CTTCCGTGCCGCAGCT
(SEQ ID NO:40) (3)

CTTCCGTGCCGGAGCT
(SEQ ID NO:41) (1)

CTTCGGTGCCGCAGCT
(SEQ ID NO:42) (1)

CTTCTGTGGCGAAGCT
(SEQ ID NO:43) (1)

GATCCGTGCCGTAGCT
(SEQ ID NO:44) (1)

GCTCTGTGCCGAAGCT
(SEQ ID NO:45) (1)

GCTGGGTGCCCAAGCT
(SEQ ID NO:46) (1)

GGTCCGTGCCGCAGCT
(SEQ ID NO:47) (1)

GGTGCTCTTCGGAGCT
(SEQ ID NO:48) (2)

GTAAACGATGGAAGCT
(SEQ ID NO:49) (1)

GTGGCTGTCGTCAGCT
(SEQ ID NO:50) (2)

GTTCCGTGCCGAAGCT
(SEQ ID NO:51) (2)

GTTCCGTGCCGCAGCT
(SEQ ID NO:52) (3)

TATCAGTGGCGCAGCT
(SEQ ID NO:53) (1)

TCTCCGTGCCGCAGCT
(SEQ ID NO:54) (1)

TCTCTGTGCCGCAGCT
(SEQ ID NO:55) (2)

TCTCTGTGCCGTAGCT
(SEQ ID NO:56) (1)

TGTCCGTGCCGTAGCT
(SEQ ID NO:57) (1)

TTTCCGTGCCGCAGCT
(SEQ ID NO:58) (2)

FIG. 15

ACGATGATAACTAGCT (SEQ ID NO:59) (2)
ACGATGATGACTAGCT (SEQ ID NO:60) (1)
ACGATGGGCACTAGCT (SEQ ID NO:61) (1)
ACGGCTGTCGTCAGCT (SEQ ID NO:62) (2)
ACTACGAGCGCAAGCT (SEQ ID NO:63) (1)
ACTTAATGCGTTAGCT (SEQ ID NO:64) (1)
ATGCTAGTCTGGAGCT (SEQ ID NO:65) (8)
ATGGCTCTCGTCAGCT (SEQ ID NO:66) (1)
ATGGCTGTCGCCAGCT (SEQ ID NO:67) (3)
ATGGCTGTCGTCAGCT (SEQ ID NO:68) (70)
ATGGTTGTCGTCAGCT (SEQ ID NO:69) (2)
ATGTAGACCTGGAGCT (SEQ ID NO:70) (12)
ATTCCGTGCCGCAGCT (SEQ ID NO:71) (6)
ATTCCGTGCCGTAGCT (SEQ ID NO:72) (1)
CACAAGCGGTGGAGCT (SEQ ID NO:73) (1)
CACTAGTGGCGCAGCT (SEQ ID NO:74) (4)
CATCCGTGCCGAAGCT (SEQ ID NO:75) (1)
CCCCAGGGCCCAAGCT (SEQ ID NO:76) (1)
CCCCGGTGCCGCAGCT (SEQ ID NO:77) (1)
CCCGCGTGCCGGAGCT (SEQ ID NO:78) (1)
CCGCGGTGCCGTAGCT (SEQ ID NO:79) (1)
CCGGGTAGTCCCAGCT (SEQ ID NO:80) (4)
CCGGGTAGTCCTAGCT (SEQ ID NO:81) (1)

CCTCCGTGCCGAAGCT (SEQ ID NO:82) (2)
CCTCCGTGCCGCAGCT (SEQ ID NO:83) (2)
CCTCCGTGCCGGAGCT (SEQ ID NO:84) (1)
CCTCGTAAGGGGAGCT (SEQ ID NO:85) (1)
CCTGGGTGCCGCAGCT (SEQ ID NO:86) (1)
CCTGGTAGTCCCAGCT (SEQ ID NO:87) (2)
CCTGGTAGTCCTAGCT (SEQ ID NO:88) (1)
CCTTAGTAACGCAGCT (SEQ ID NO:89) (1)
CCTTGGTAACGAAGCT (SEQ ID NO:90) (1)
CGCCAGTGCCGAAGCT (SEQ ID NO:91) (1)
CGCCGGTGCCGCAGCT (SEQ ID NO:92) (2)
CGCCTGTGCCGTAGCT (SEQ ID NO:93) (2)
CGCTCGTGGCGAAGCT (SEQ ID NO:94) (1)
CGGAGGCGTCGTAGCT (SEQ ID NO:95) (1)
CGTCAGTGTCGCAGCT (SEQ ID NO:96) (2)
CGTCCGTGCCGAAGCT (SEQ ID NO:97) (7)
CGTCCGTGCCGCAGCT (SEQ ID NO:98) (1)
CGTCCGTGCCGGAGCT (SEQ ID NO:99) (1)
CGTCGGTGCCGCAGCT (SEQ ID NO:100) (2)
CTCCAGTGCCGCAGCT (SEQ ID NO:101) (1)
CTCCCGTGCCACAGCT (SEQ ID NO:102) (1)
CTCCCGTGCCGCAGCT (SEQ ID NO:103) (2)
CTCCCGTGCCGGAGCT (SEQ ID NO:104) (3)

CTCCGGTGCCGCAGCT (SEQ ID NO:105) (1)
CTCCTGTGCCGCAGCT (SEQ ID NO:106) (1)
CTGCCGCGCCGGAGCT (SEQ ID NO:107) (1)
CTGCCGTGCCGAAGCT (SEQ ID NO:108) (5)
CTGCCGTGCCTAAGCT (SEQ ID NO:109) (1)
CTGCGGTGCCGCAGCT (SEQ ID NO:110) (1)
CTGCTGTGCCGAAGCT (SEQ ID NO:111) (7)
CTGTCGTGCCGAAGCT (SEQ ID NO:112) (1)
CTTCCGCGCCGGAGCT (SEQ ID NO:113) (7)
CTTCCGTGCCGAAGCT (SEQ ID NO:114) (2)
CTTCCGTGCCGCAGCT (SEQ ID NO:115) (6)
CTTCCGTGCCGGAGCT (SEQ ID NO:116) (2)
CTTCGGTGCCGCAGCT (SEQ ID NO:117) (1)
CTTCGGTGTCGCAGCT (SEQ ID NO:118) (1)
CTTGGGTGCCGCAGCT (SEQ ID NO:119) (2)
CTTTAGTAACGCAGCT (SEQ ID NO:120) (2)
GACCCGCAAGGGAGCT (SEQ ID NO:121) (1)
GATCCGTGCCGCAGCT (SEQ ID NO:122) (2)
GCTCCGTGCCGAAGCT (SEQ ID NO:123) (1)
GCTCCGTGCCGTAGCT (SEQ ID NO:124) (1)
GCTCTGTGCCGAAGCT (SEQ ID NO:125) (2)
GCTCTGTGCCGTAGCT (SEQ ID NO:126) (1)
GGGCTTGTCGTCAGCT (SEQ ID NO:127) (1)
GTAAACGATGGAAGCT (SEQ ID NO:128) (1)
GTTCCGTGCCGCAGCT (SEQ ID NO:129) (2)
GTTCCGTGCCGTAGCT (SEQ ID NO:130) (2)
GTTCTGTGCCGCAGCT (SEQ ID NO:131) (2)
TCTCACGACACGAGCT (SEQ ID NO:132) (2)
TCTCAGTAACGTAGCT (SEQ ID NO:133) (1)
TCTCCGTGCCGCAGCT (SEQ ID NO:134) (2)
TCTCTGTGCCGCAGCT (SEQ ID NO:135) (4)
TGGACGTTGCGGAGCT (SEQ ID NO:136) (2)
TTTCCGTGCCGGAGCT (SEQ ID NO:137) (1)

FIG. 16

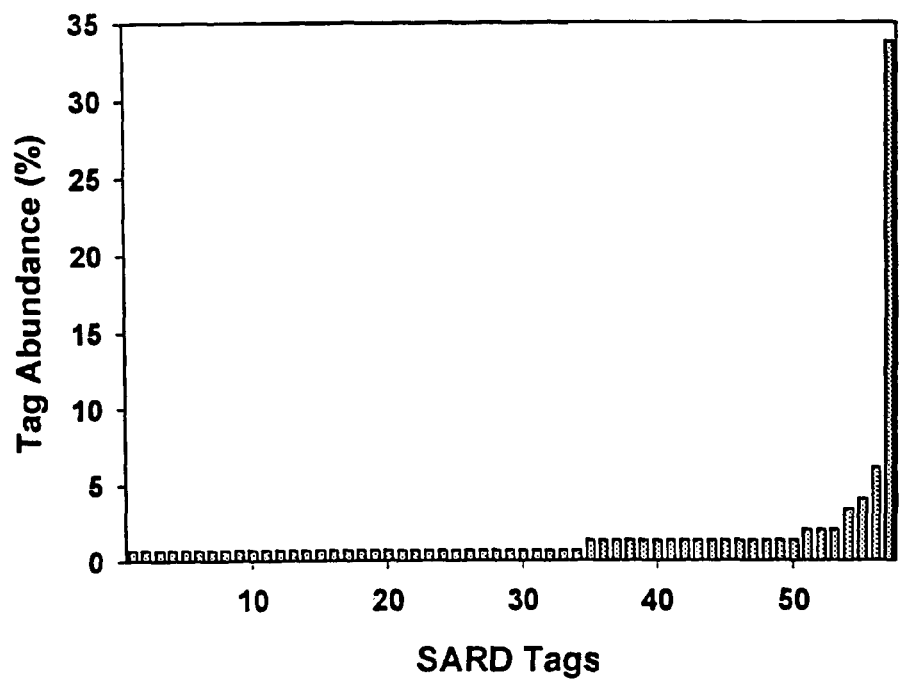
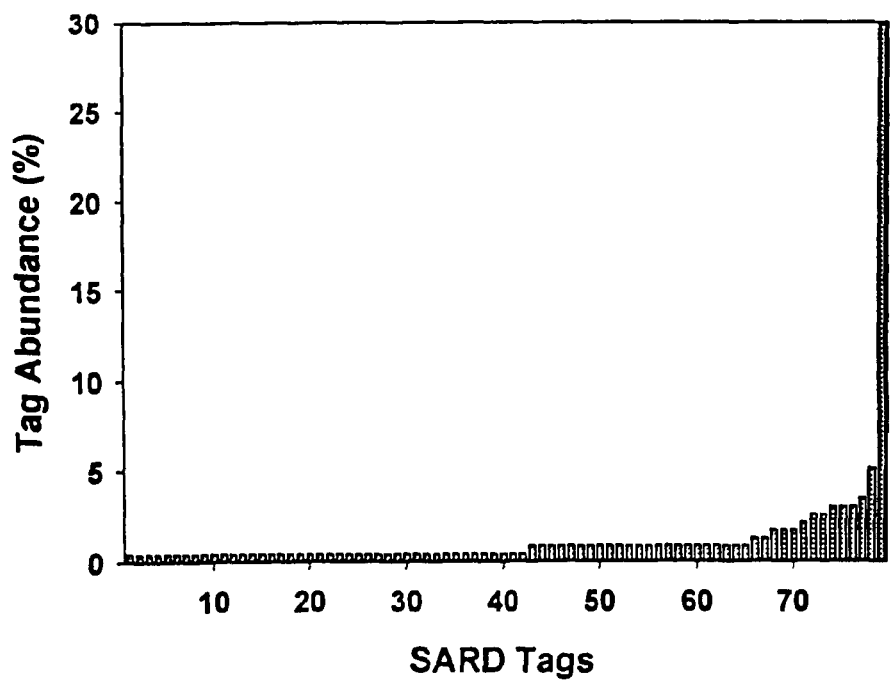
FIG. 17

DNA-BASED METHODS OF GEOCHEMICAL PROSPECTING

This application is a divisional of application Ser. No. 09/829,855, filed Apr. 10, 2001, which in turn claims the benefit of U.S. provisional application Ser. No. 60/196,063, filed Apr. 10, 2000 and U.S. provisional application Ser. No. 60/196,258, filed Apr. 11, 2000.

This Invention was made with Government support under Contract No. DE-FC36-01G011016 awarded by the Department of Energy. The Government has certain rights in this invention.

TECHNICAL FIELD OF THE INVENTION

The present invention relates to methods for performing surveys of the genetic diversity of a population. The invention also relates to methods for performing genetic analyses of a population. The invention further relates to methods for the creation of databases comprising the survey information and the databases created by these methods. The invention also relates to methods for analyzing the information to correlate the presence of nucleic acid markers with desired parameters in a sample. These methods have application in the fields of geochemical exploration, agriculture, bioremediation, environmental analysis, clinical microbiology, forensic science and medicine.

BACKGROUND OF THE INVENTION

Microbes have been used previously as biosensors to identify chemicals in the environment. For instance, microbes have been utilized as biosensors for the presence of nitrates (Larsen, L. H. et al., 1997, A microscale $NO_3$ biosensor for environmental applications. *Anal Chem.* 69:3527-3531), metals (Virta M. et al., 1998, Bioluminescence-based metal detectors. *Methods Mol. Biol.* 102:219-229), and a variety of hydrocarbons (Sticher P. et al., 1997, Development and characterization of a whole-cell bioluminescent sensor for bioavailable middle-chain alkanes in contaminated groundwater samples. *Appl. Environ. Microbiol.* 63(10):4053-4060). In these examples however, the indicator microbes are not native species, but rather, the product of recombinant manipulations designed for specific applications. These modifications involve coupling the nutrient sensing machinery of well-characterized bacterial strains with reporter genes to aid identification. This approach is limited, however, by the metabolic diversity of a few well-characterized bacterial strains. In contrast, the large and diverse pool of microbes in the environment represents a source of biosensors for a much larger range of applications than currently exists. Thus, there is a need to identify and use other microbes, especially those found in situ, as biosensors.

Microbes also have an important impact on health and medicine. Estimates have been made there may ten times the number of microbial cells associated with the human body as there are human cells. Many microbial cell populations that are associated with the human body play a beneficial role in maintaining health. For instance, gut microflora is important for proper digestion and absorption of nutrients and for production of certain factors, including some vitamins. In general, the human immune system is able to keep the bacterial populations of the human body in check and prevent the overgrowth of beneficial microbial populations and infection by detrimental microbial populations. Nevertheless, the list of human diseases that are now attributed to microbial pathogens is growing. However, nearly all of the information regarding the relationships between microbes and human disease have been gained from approaches that require culture of microbial species.

Two examples of diseases where the causative agents were identified through molecular methods include bacillary angiomatosis (Relman, D. A. et al., 25 1990, New Engl. J. Med. 323: 1573) and Whipple's disease (Wilson, K. H. et al., 1991, Lancet 338: 474). Further, the central aspects of atherosclerosis are consistent with the inflammation that results from infection. DNA sequences from *Chlamydia* have been identified from atherosclerotic lesions and has led to suggestions that this organism plays a role in the disease.

In addition, bacterial infections have become an increasing health problem because of the advent of antibiotic-resistant strains of bacteria. Further, microbial infections caused by bacteria or fungi that do not usually infect humans may be a problem in immunocompromised individuals. Further, individuals in developing countries who may be malnourished or lack adequate sanitary facilities may also support a large load of opportunistic bacteria, many of which may cause sickness and disease. In veterinary medicine, livestock living in close quarters also may be prey to infections caused by a variety of different types of microbes. Thus, there is a need to develop sensitive methods of identifying many different types of microbes without having to cultivate them first in order to treat or prevent microbial infections in humans and other animals.

Assays for microbial contamination is an important component of food testing as well. A large number of different types of microbes may contaminate food for humans or animals. Thus, an ability to test food for contamination quickly and effectively is critical for maintaining food safety. However, many of the microbes responsible for causing sickness in humans and animals are difficult to isolate or identify.

Assays for microbial populations also has use in fields such as forensic science. Over the past ten to twenty years, scientists have determined that microbial populations change when bodies begin to decay, and have begun to identify certain microbial species that are indicative of decomposition (Lawrence Osborne, Crime-Scene Forensics; Dead Men Talking, *New York Times*, Dec. 3, 2000). However, only a few microbial species that may be useful in these analyses. has been identified.

The problem of determining genetic diversity is not confined to microbial populations. Antibody diversity is critical for a proper immune response. During B cell differentiation, antibody diversity is generated in the heavy and light chains of the immunoglobulin by mechanisms including multiple germ line variable (V) genes, recombination of V gene segments with joining (J) gene segments (V-J recombination) and recombination of V gene segments with D gene segments and J gene segments (V-D-J recombination) as well as recombinational inaccuracies. Furthermore, somatic point mutations that occur during the lifetime of the individual also lead to antibody diversity. Thus, a huge number of different antibody genes coding for antibodies with exquisite specificity can be generated. T cell receptor (TCR) diversity is generated in a similar fashion through recombination between numerous V, D and J segments and recombinational inaccuracies. It has been estimated that $10^{14}$ Vδ chains, more than $10^{13}$ β chains and more than $10^{12}$ forms of Vα chains can be made (Roitt, I. et al., Immunology, 3rd Ed., 1993, pages 5.1-5.14). A knowledge of the antibody or TCR diversity in a particular individual would be useful for diagnosis of disease, such as autoimmune disease, or for potential treatment.

The identification of microbes, especially soil microbes, has traditionally relied upon culture-dependent methods, whereby the detection of a microbial species depends upon the ability to find laboratory conditions that support its growth. To this end, 96-well plates have been commercially developed to identify microbes with different metabolic requirements. For instance, BioLog plates incorporate 96 different media formulations into the wells of a 96-well plate. Despite these efforts, it is now accepted that far fewer than 1% of microbes can propagate under laboratory conditions (Amann, R. I. et al., 1995. Phylogenetic identification and in situ detection of individual microbial cells without cultivation. *Microbiol. Rev.* 59:143-169).

The widespread interest in genomics has created many exciting new technologies for the parallel quantitation of thousands of distinct nucleic acid sequences simultaneously. While still in their infancy, these technologies have provided unprecedented insight into biology. To date, these technologies have predominately been utilized in pharmaceutical and agricultural applications. Genome expression profiling has gained general acceptance in biology and is likely to become commonplace in all academic, biotechnology and pharmaceutical institutions in the $21^{st}$ century. For instance, Serial Analysis of Gene Expression (SAGE) is a hybridization-independent method designed to quantitate changes in gene expression (Velculescu, V. E. et al., 1995, Serial analysis of gene expression. *Science* 270:484-487 and U.S. Pat. No. 5,866,330). However, SAGE only measures RNA levels from tissues or organisms, and is not suitable for examining genetic diversity.

The widespread interest in genomics has also led to the development of many technologies for the rapid analysis of tens of thousands of nucleic acid sequences. One such technology is the DNA chip. Although this approach had been used as a diagnostic for distinguishing between several species of the genus *Mycobacterium* (Troesch, A., et al., 1999, *Mycobacterium* species identification and rifampin resistance testing with high-density DNA probe arrays. *J. Clin. Microbiol.* 37:49-55), it has limited utility for an environmental microbial survey for two reasons. First, the sequence of the target DNAs to be analyzed must be known in order to synthesize the complementary probes on the chip. However, the vast majority of environmental microbes have not been characterized. Second, DNA chips rely on hybridization of nucleic acids which is subject to cross hybridization from DNA molecules with similar sequence. However, the resolving power of a hybridization-based approach is limited because one must identify regions of DNA that do not cross-hybridize, which may be difficult for related microbial species.

Genomic technologies and bioinformatics hold much untapped potential for application in other areas of biology, especially in the field of microbiology. However, to date there has not been a method to rapidly and easily determine the genomic diversity of a population, such as a microbial or viral population. Further, there has not been a method to easily determine the antibody or TCR diversity of a population of B or T cells, respectively. Thus, there remains a need to develop such methods in these areas.

BRIEF SUMMARY OF THE INVENTION

The present invention solves this problem by providing methods for rapidly determining the diversity of a microbial or viral population and for determining the antibody or TCR diversity of a population of B or T cells. The present invention relies on hybridization-independent genomic technology to quickly "capture" a portion of a designated polymorphic region from a given DNA molecule present in a population of organisms or cells. This portion of the DNA molecule, a "marker," is characteristic of a particular genome in the population of interest. The marker can be easily manipulated by standard molecular biological techniques and sequenced. The sequence of a multitude of markers provides a measure of the diversity and/or identity of a population. In one aspect, the invention provides a method, Serial Analysis of Ribosomal DNA (SARD), that can be used to distinguish different, members of a microbial population of interest.

In another aspect, the invention provides a method for analyzing a designated polymorphic region from a population of related viruses using method steps similar to those described for SARD. In a further aspect, the invention provides a method for analyzing the variable regions from the immunoglobulins or TCR genes of a population of immune cells using methods steps similar to those described for SARD.

In another aspect of the invention, a method is provided for analyzing a population based upon an array of the masses of peptides that are encoded by polymorphic sequences of particular DNA molecules in a region of interest. In a preferred embodiment, the region of interest is a designated polymorphic region from an rDNA gene from each member of a microbial population.

In another aspect of the invention, a method is provided for analyzing the information provided by the above-described methods. The method enables the creation of a diversity profile for a given population. A collection of diversity profiles provides an accurate representation of the members present in a population. These diversity profiles can be entered into a database along with other information about the population. The diversity profiles can be used with various correlation analyses to identify individual, or sets of individuals that correlate with each other. The correlation analyses can be used for diagnostic or other purposes. In another aspect, the invention provides databases comprising various diversity profiles. In a preferred embodiment, the diversity profile. is obtained by SARD.

In yet another aspect of the invention, a method is provided for identifying a diversity profile, as described above, that correlates with a parameter of interest. In a preferred embodiment, the diversity profile is a profile of the microbial populations that correlate with the presence of mineral deposits and/or petroleum reserves. In another preferred embodiment, the diversity profile is a profile of populations of different antibodies or TCR that correlate with a specific disease state, such as an autoimmune disorder.

In a still further aspect, the invention provides a method for locating mineral deposits or petroleum reserves comprising identifying one or more nucleic acid markers that correlate with the presence or mineral deposits or petroleum reserves, isolating nucleic acid molecules from an environmental sample, determining whether the nucleic acid markers are present in the environmental sample, wherein if the nucleic acid markers are present, then the area from which the environmental sample was obtained is likely to have mineral deposits or petroleum reserves.

BRIEF DESCRIPTION OF THE DRAWINGS

FIG. 3 shows a number of representative members of the domain Bacteria with their taxonomic relationships.

FIG. 4 shows a number of representative members of the domain Archaea with their taxonomic relationships.

FIG. 7A: Significant correlation with all markers within the MDP. FIG. 7B: No correlation found using all the markers within the MDP. FIG. 7C: Same plot as B except that significant correlation is found using a subset of markers.

Figure 1:
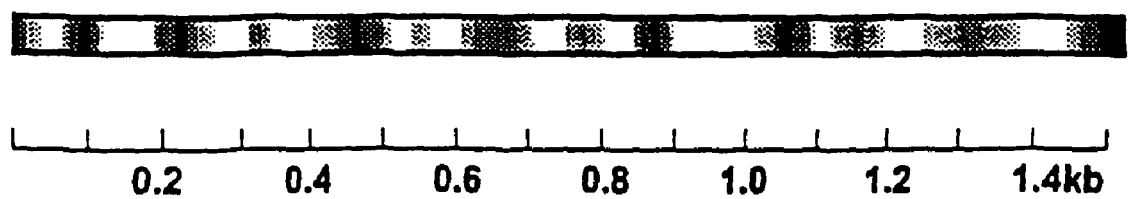
FIG. 1 shows a representation of a 16S rDNA gene from Bacteria illustrating polymorphic regions (shown as dark bands) and constant regions (shown as light bands).

If the query in decision block 210 returns a "No" the routine proceeds to decision block 220 which queries whether the new marker diversity profile is a subset of a resident profile in the database. If the query returns a "No" the parameters remain undefined 225. If the query returns a "Yes" the routine proceeds to step 230. Step 230 is an optional step to determine the correlation between members of the common subset of markers and may either be performed for each new profile or may be queried from a matrix table of pre-calculated values from existing profiles. Such values generally would be maintained in a relational database. If this step is not performed all common markers are parsed into groups of individual markers and treated as correlated groups 255. If the marker-marker correlation is performed between the common subset of markers, the routine proceeds to decision block 235 which queries whether all of the common markers are correlated. If the query returns a "Yes" the markers are correlated with the parameters 240 resident in the database. If none of the markers are correlated with a parameter, the parameter(s) remain undefined 245 whereas if the markers are correlated with a parameter, the parameter is deduced to be associated with the marker diversity profile 250. If the decision block query 235 returns a "No", the common markers are sorted into groups of correlated markers 255. The first correlated marker group N 260 is subject to a decision block 265 that queries whether the markers in this group are correlated with a parameter. A "No" determines that the parameters remain undefined. If the marker(s) are correlated with a parameter, the parameter is deduced to be associated with the marker diversity profile. Steps 260-275 are repeated in steps 280-295 for each correlated group of markers. The groups of correlated markers may be comprised of a single or multiple markers. The confidence level in deducing that a parameter is associated with a marker diversity profile is determined by the level of correlation between the marker(s) and the parameter. Therefore, sets of correlated markers are expected to be more robust indicators of any given parameter.

Figure 10:
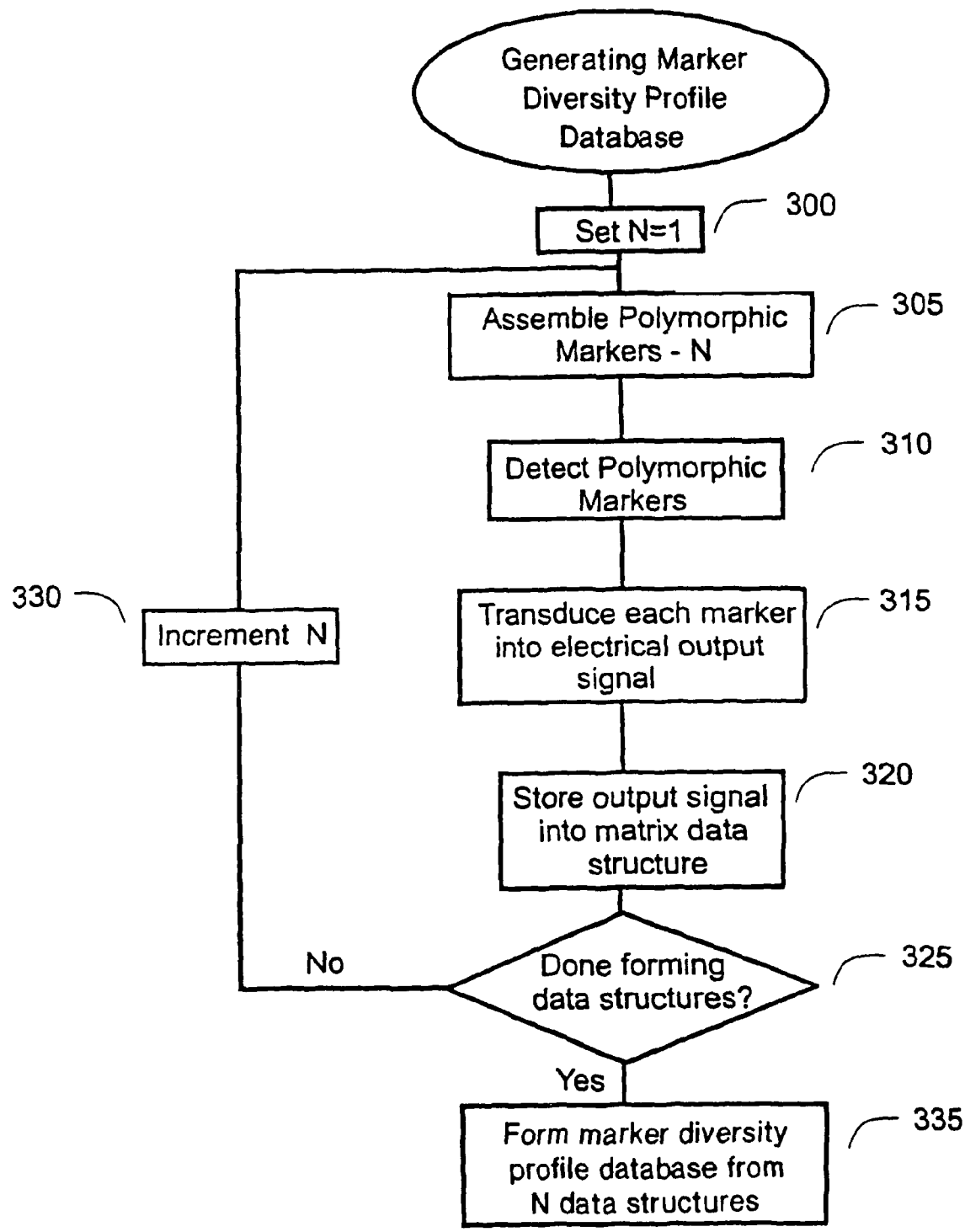

FIG. 10 shows a schematic for generating a marker diversity profile matrix database. The first step 300 involves assigning N an integer value of 1 corresponding to the first MDP data structure. The second step 305 involves assembling polymorphic markers from a sample. Examples of methods for assembling such markers are described in this application and include, but are not limited to, SARD (FIG. 2, Tables I and II) or mass tag compilation (Table III). The next step 310 involves detecting the polymorphic markers. Examples of methods to detect polymorphic markers described above include DNA sequence analysis of SARD tags and MALDI-TOF analysis of mass tags, respectively. The next step 315 involves the conversion or transduction of the MDP into an electrical signal output. Generally, this process is a linear electronic conversion of the data into a digital signal. Step 320 involves storing into the memory of a computer the output signal from each MDP into a matrix data structure associating each MDP with a geographic coordinates such as longitude and latitude. The next step is a decision block 325 where if all the data structures have not been completed the routine advances to step 330 where n is incremented and the data structure, generating steps 305-320 are repeated for the n+1$^{th}$ marker diversity profile. Once all the data structures are completed the routine proceed to step 335 to form the MDP database from n data structures. Each marker is assigned a unique identifier and indexed with its relative abundance in the population. These signals are digitized and stored in the memory of a computer.

Figure 11:
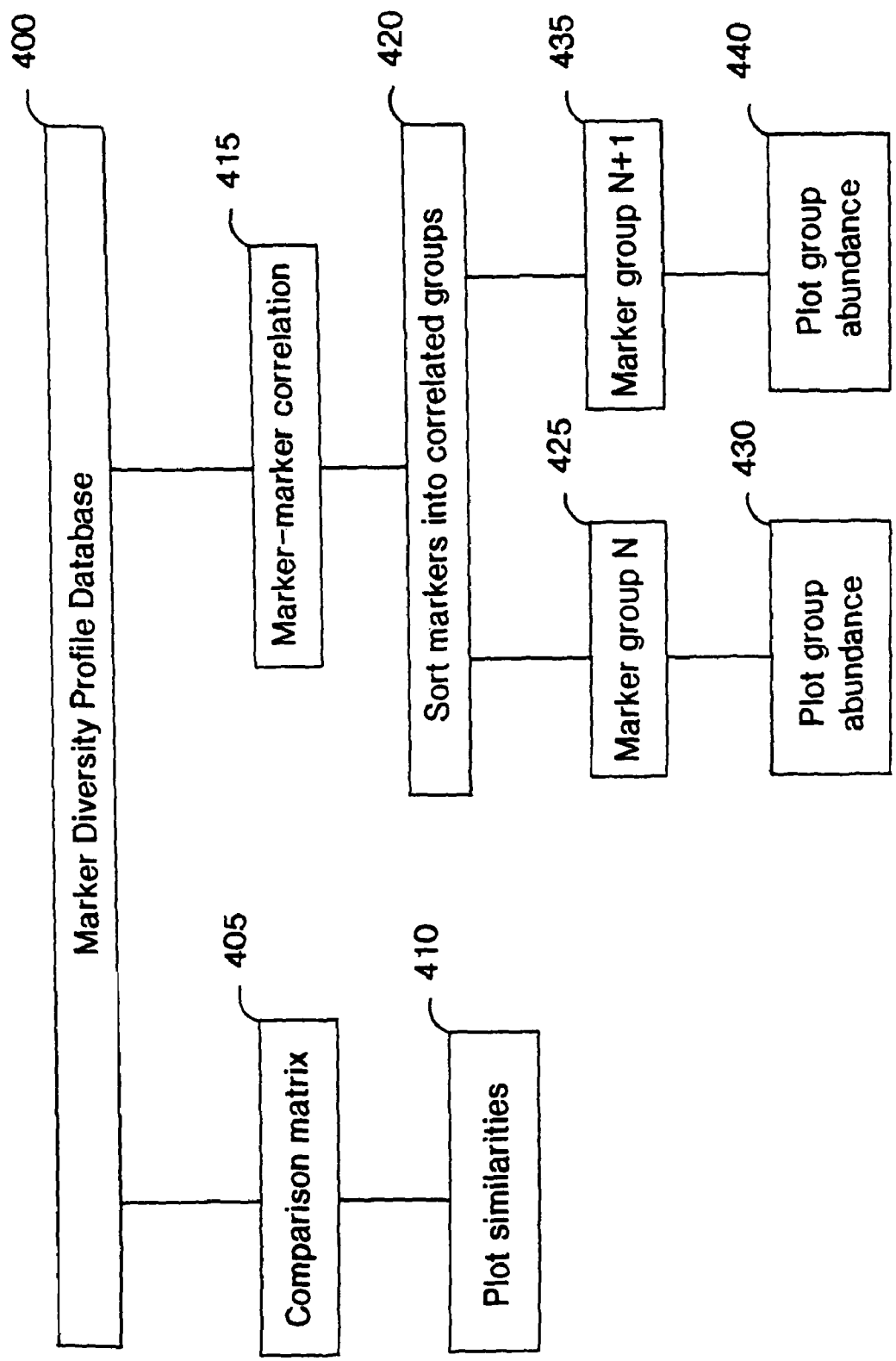

FIG. 11 shows a schematic for mapping applications using marker diversity profiles. Marker diversity profile data 400 can be processed in several ways to create maps that provides significant environmental information. In one example 405, each marker diversity profile in a database can be correlated with every other marker diversity profile in a pairwise manner to create a correlation matrix. By appending this data to the geographical coordinates of each sample 410, a map can be constructed that reflects the correlation values of physically neighboring sample sites. Preferably the correlation values will be color coded to reflect the level of correlation. The color is chosen from a reference color spectrum that is indexed to correlation values between 0-1.

Marker diversity profiles 400 can also, be processed into maps at the individual marker or correlated marker group level. This approach is preferable since subsets of markers are likely to correlated to fewer number of sample associated parameters. Each marker in a marker diversity profile database is correlated with every other marker in the database in a pairwise manner to create a correlation matrix 415. The source database can either be composed of marker diversity profiles from a single geographic area or several distinct areas. In step 420, the markers from one geographic area are sorted into groups based upon their level of correlation. In step 425, the relative representation of the correlated marker group N is determined along with its geographical coordinates for each marker diversity profile in a geographic area. A map is constructed 430 where the relative abundance of each correlated marker group is color-coded with its geographical coordinates. Steps 425 and 430 are repeated as in 435 and 440 for each correlated group of markers.

FIG. 12 shows oligonucleotides useful for amplifying nucleic acid molecules for SARD.

FIG. 13 shows the use of the SARD strategy for Eubacteria. The double-underlined sequence and the wavy-underlined sequence represent the sequence tags for the two pools and the single-underlined sequence delineates the BpmI recognition site.

Figure 14:
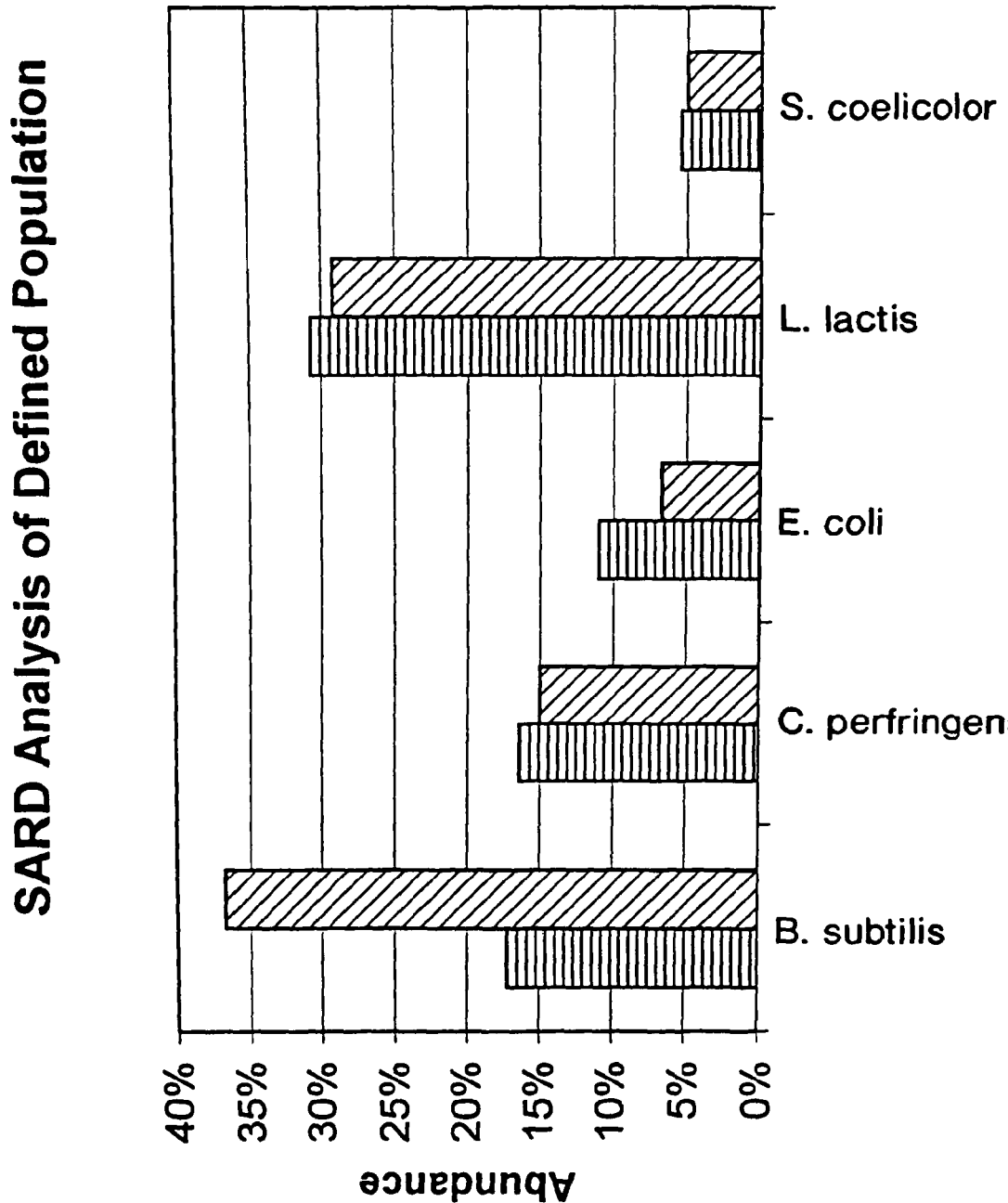

FIG. 14 is a graphical representation of a SARD analysis of a defined population.

FIG. 15 shows the sequence of SARD tags identified from Wy-1 sample. The number in parentheses indicates the number of tags having that sequence.

FIG. 16 shows SARD tags identified from Wy-2 sample. The number in parentheses indicates the number of tags having that sequence.

FIG. 17 is a graphical representation of the number and abundance of SARD tags. The upper panel shows the Wy-1 SARD Tag Diversity Profile and the lower panel shows the Wy-2 SARD Tag Diversity Profile.

DETAILED DESCRIPTION OF THE INVENTION

The extent of the diversity of microbes in our environment has only recently been recognized. With the advent of the polymerase reaction (PCR) and small subunit ribosomal DNA (rDNA) sequence analysis, researchers have been able to detect and perform phylogenetic analyses on individual microbes without first cultivating the microbes of interest. This molecular phylogenetic approach has significantly changed.our view of microbial evolution and diversity (Woese, C. R., 1987, Bacterial evolution. *Microbiol Rev.* 51(2):221-71; Pace, N. R., 1997, A molecular view of microbial diversity and the biosphere. *Science.* 276(5313):734-40). For instance, the earliest life forms are now thought to have utilized inorganic compounds for nutrition rather than compounds based upon organic carbon. In addition, the vast proportion of biological diversity is now known to be due to microbial species. Estimates have been made that there may be more than ten thousand distinct species of microbes in a single gram of soil. FIGS. 3 and 4 show some of the representative members of the domains Bacteria and Archaea, respectively, that may be found in environmental samples.

Microbes inhabit virtually all niches including extreme environments with temperatures between 20° and 250° F. Microbes have even been isolated from deep petroleum reservoirs more than a mile beneath the earth's surface (Jeanthon, C. et al., 1995, *Thermotoga subterranea* sp. nov., a new thermophilic bacterium isolated from a continental oil reservoir. *Arch. Microbiol.* 164:91-97). In order to prevail under such diverse conditions, microbes have made remarkable adaptations and have attained the ability to utilize unusual carbon and mineral resources that are immediately available. These physiological and metabolic adaptations that enable some microbes to inhabit a particular niche may also restrict their distribution to such areas. Numerous examples of environmental parameters that lead to restrictions of microbial distribution are well known and are usually dictated by a species' specific metabolic program (e.g. obligate nature of the carbon, nitrogen and energy source).

Microbes that have highly defined nutrient requirements are likely to have a restricted distribution in the environment. Thus, the microbes' dependence on the presence of a particular resource to proliferate can serve as the basis for an assay to identify the presence, and characterize the distribution, of various features in the environment, such as biological, chemical and geochemical features. In other words, microbes can function as environmental biosensors.

In one aspect of this invention, the ability of microbes to function as environmental biosensors is used to identify particular environmental states. In a preferred embodiment, a profile of a microbial population is used to identify one or more parameters of a particular environmental state. In a more preferred embodiment, a microbial population profile is used to identify areas that are likely to have mineral deposits and/or petroleum reserves. In another preferred embodiment, a microbial population profile is used in forensic science to identify decomposition of a body or to associate an individual to another individual, to an object or to a location. In yet another preferred embodiment, a microbial population profile is used to identify microbial contamination of human and animal foodstocks. In yet another preferred embodiment, the profile is used to diagnose human or animal disease.

Definitions

Unless otherwise defined, all technical and scientific terms used herein have the meaning as commonly understood by one of ordinary skill in the art to which this invention belongs. The practice of the present invention employs, unless otherwise indicated, conventional techniques of chemistry, molecular biology, microbiology, recombinant DNA, genetics and immunology. See, e.g., Maniatis et al., 1982; Sambrook et al., 1989; Ausubel et al., 1992; Glover, 1985; Anand, 1992; Guthrie and Fink, 1991 (which are incorporated herein by reference).

A microbe is defined as any microorganism that is of the domains Bacteria, Eukarya or Archaea. Microbes include, without limitation, bacteria, fungi, nematodes, protozoans, archaebacteria, algae, dinoflagellates, molds, bacteriophages, mycoplasma, viruses and viroids.

A marker is a DNA sequence that can be used to distinguish or identify a particular gene, genome or organism from another. In one embodiment, a marker may be generated by one of the methods described herein. A marker represents one or a limited number of taxonomic species or genes. In a preferred embodiment, a marker represents a single taxonomic species or gene. In one embodiment, the marker represents a single microbial species. In another embodiment, the marker represents a single viral species or type. In another embodiment, the marker represents a single immunoglobulin or TCR variable domain.

A marker diversity profile (NMP) is a data set that is obtained from each population sample and that contains a collection of markers. In a preferred embodiment, the MDP also comprises other information, including all known parameters associated with a particular population sample. Such parameters that relate to environmental samples may include inorganic components (obtained through atomic adsorption analysis), organic components (obtained through GC-MS or LC-MS), grain size analysis, pH, and salinity. Parameters that relate to medical samples would include, but are not limited to, a complete medical history of the donor. In a preferred embodiment, the markers are obtained by SARD.

Methods for the Genetic Analysis of Populations

Ribosomes, which are comprised of numerous ribosomal proteins and three ribosomal RNA (rRNA) molecules, are a key component of protein synthesis. The 16S subunit rRNA, which is encoded by the 16S rDNA gene, has been the focus of much attention in microbial phylogenetic studies. The 16S rDNA sequence is highly conserved between taxonomic groups, yet also possesses regions that are highly polymorphic (FIG. 1). Moreover, the rate of change in the RNA sequence is thought to have been relatively constant over evolutionary time, enabling scientists to determine the relative relatedness of different organisms.

Typical molecular microbial analyses involve utilizing the highly conserved regions of the 16S rDNA to amplify the roughly 1,500 bp gene. The sequence of the PCR-amplified product is determined and compared with other known rDNA sequences. Although this approach is highly informative, it is not amenable to a rapid survey of an environmental microbial community.

The instant invention provides methods for quickly and easily calculating the genetic diversity of a population. The methods uses hybridization-independent genomic technologies to overcome the previously-identified problems of determining genetic diversity. This method may be used for any population of cells, viruses or organisms which comprise at least one DNA molecule that comprises regions of high sequence conservation interspersed with polymorphic sequences, wherein the polymorphic sequences can be used to distinguish different members of the population of interest. One aspect of the present invention describes a method (SARD) that can capture a designated polymorphic region from a given DNA molecule present in the members of a microbial community. In a preferred embodiment, the DNA molecule is a 16S rDNA molecule. In another embodiment, the DNA molecule is the intergenic region between the 16S and 23S rDNA genes. In another embodiment, the method is used to identify the genetic diversity of a population of viral samples or of cells or organisms infected with a population of viruses. In another embodiment, the method is used to identify the diversity of immunoglobulin and/TAR genes in a population of B and/or T cells.

The method may be performed as follows (see FIG. 2):

Step I. Sample Preparation and DNA Amplification by PCR

Samples may be obtained from any organism or region desired. For environmental microbial analyses, samples may be obtained from, without limitation, buildings, roadways, soil, rock, plants, animals, cell or tissue culture, organic debris, air or water. For medical microbial analyses, samples may be obtained from, without limitation, humans, animals, parasites, water, soil, air and foodstuffs. For viral analyses, samples may be obtained from, without limitation, viral culture stocks, humans, animals, plants, cell or tissue culture and microbes. For immunoglobulin or TCR analyses, samples may be obtained from, without limitation, humans, animals or cell or tissue cultures. DNA molecules from the sample of interest may be isolated by any method known in the art. See, e.g., Sambrook et al., 1989 and Ausubel et al., 1992. In a preferred embodiment, DNA is obtained as described by Yeates et al., "Methods for Microbiological DNA Extraction from Soil for PCR Amplification," Biological Procedures Online, Volume 1, May 14, 1998, available through the Internet; Liu et al., Applied and Environmental Microbiology (1997) 63: 4516-4522; and Tsai et al., Applied and Environmental Microbiology (1992) 58: 2292-2295. The DNA molecules do not have to be completely purified but only need be isolated to the point at which PCR may be performed.

Environmental microbes often exist in biofilms (Costerton, J. W., et al., 1999, Bacterial biofilms: a common cause of persistent infections. *Science* 284(5418):1318-1322) or in tight association with solid surfaces. Microbial DNA from a sample of interest is isolated by one of several methods that are widely known to those skilled in the art and are described in the literature (Gillan, D. C. et al., 1998, Genetic diversity of the biofilm covering *Montacuta ferruginosa* (Mollusca, bivalvia) as evaluated by denaturing gradient gel electrophoresis analysis and cloning of PCR-amplified gene fragments coding for 16S rRNA. *Appl Environ. Microbiol.* 64(9): 3464-72).

The samples may be selectively enriched before they are isolated by any method known in the art. In one embodiment, for a population of microbes that are known or suspected to feed on a hydrocarbon source such as propane, the hydrocarbon may be added to the environment in which the microbes live for a period of time before the microbes are harvested. In another embodiment, a viral population may be cultivated in cells before they are isolated. In a further embodiment, B and T cells may be expanded in culture before isolation. It may be easier to obtain sufficient sample amounts if a population is expanded before isolation. However, this must be weighed against the possibility that expansion will alter the ratio of different members of the population to each other.

In general, the primers used for amplification are designed to hybridize to a region of the DNA that is highly conserved between members of the population. Further, the primers should flank a polymorphic region the partial sequence of which should provide diagnostic information regarding the genetic diversity of the population. For instance, for the 16S rDNA gene, primers are designed to hybridize to a highly conserved region of the 16S rDNA gene flanking a polymorphic region (see FIG. 2). In an immunoglobulin gene, the primers are designed to hybridize to a region of the B cell DNA flanking the V-J recombination site. Alternatively, primers may be designed that bind to the relatively constant regions within certain regions of the V-J gene that flank a polymorphic region. See Roitt et al., *Immunology*, 3rd Ed., 1993, pp. 5.2-5.14, herein incorporated by reference, which shows regions of variability and conservation within immunoglobulin and TCR genes. One having ordinary skill in the art following the teachings of the specification will recognize that other genes that have regions that are highly conserved between members of the population and that flank polymorphic regions may be used in the design of primers.

The primers should also be designed to flank a region of DNA that comprises a restriction site for a restriction enzyme. In a preferred embodiment, the restriction enzyme is a cuts at a four-basepair recognition site, such as AluI (see FIG. 2). Furthermore, the restriction site should be near but not in the polymorphic region of the gene of interest. In a preferred embodiment, the restriction site should be one that is present in the gene of interest in a majority of the known species or genes.

A single set of primers may be used or multiple sets of primers may be used. A single set of primers may be used if it is known that the region of DNA to which the primers will bind is very highly conserved. Alternatively, if it is known that there is some variation in the conserved region, multiple sets of primers may be used to bind to the conserved DNA region. Using multiple sets of primers may be useful to identify more members of a population, especially those members of the population that exhibit less sequence identity in the conserved areas of a nucleic acid sequence. In one embodiment, four to ten sets of primers may be used to identify members of a population. Alternatively, the primers used may be degenerate, such that different molecules within a primer population will include a different base at one or more specific sites in the primer. For instance, a primer may have a site that has either cytosine or thymidine. The purpose of making primers degenerate is to increase the number of different DNA molecules that will hybridize to a particular primer. Methods of making degenerate primers are well-known in the art.

The primers used in this and in subsequent steps are generally of a length sufficient to promote specific hybridization to a DNA sequence. The primers generally have a length of at least 12 bases, more preferably at least 15 bases, even more preferably at least 18 bases. The primers may have a length of up to 60 bases, although usually most are under 40 bases in length. Primers may include both bases that are naturally found in DNA, such as adenine, guanine, cytosine and thymidine, and may also include nucleotides that are not usually found in DNA, such as inosine.

One of the primers (the "upstream" primer) should be modified to incorporate a moiety that can be used to bind the PCR product to a solid support. The upstream primer is defined as the primer that is located on the opposite side of the polymorphic region of interest relative to the flanking four-base restriction site. A number of different binding moieties are known in the art. In a preferred embodiment, the moiety is biotin. In another preferred embodiment, the moiety is digoxigenin or six histidines.

PCR is performed using the primers to amplify a subregion that contains a polymorphic site of interest. Methods for performing PCR are well-known in the art. In one embodiment, the PCR products are normalized or subtracted by methods known in the art to lower the representation of the dominant sequences. Exemplary methods are described in Sambrook et al., 1989, Ausubel et al., 1992; Glover, 1985; Anand, 1992 (which are incorporated herein by reference).

Step II. Digestion of the Amplified Fragment and Binding to Solid Support

Figure 2:
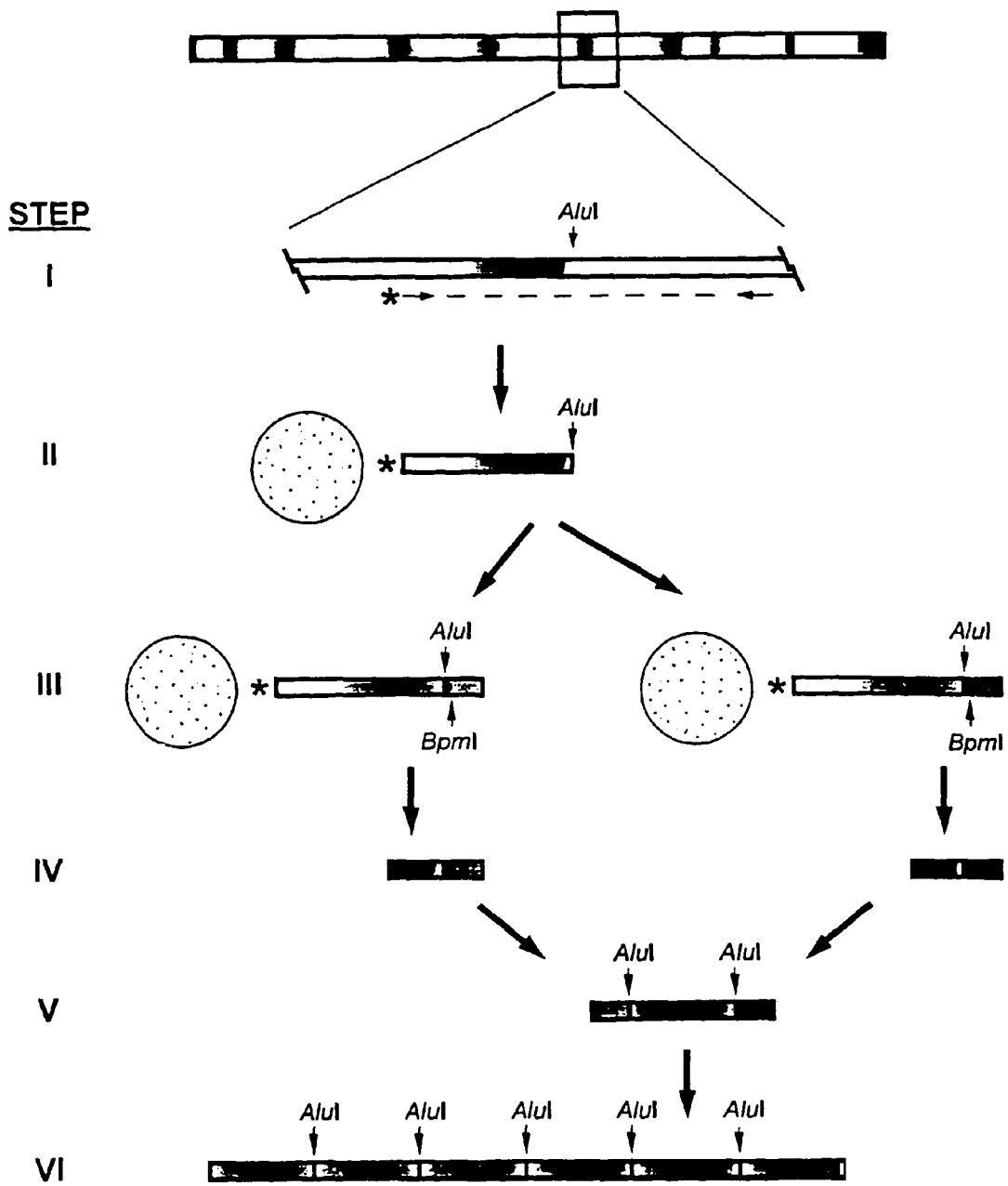
FIG. 2 shows a schematic representation of the SARD method for isolating polymorphic sequence tags from Bacterial rDNA.

The amplified fragment is cut with the restriction enzyme as discussed in Step I. Any restriction enzyme may be used in this step so long as it is cuts at a site immediately adjacent to the polymorphic sequence. In a preferred embodiment, the enzyme is a four-base restriction enzyme. Examples of four-base restriction enzymes are well-known in the art and include many that are commercially available. See, e.g., New England Biolabs Catalog 2000, herein incorporated by reference. Examples of four-base restriction enzymes include, without limitation, AluI, Bsh1236I, DpnI, HpaII, MboI, MspI, PafI (an isoschizomer of HaeIII), RsaI, Sau3AI and TaqI. After restriction, the DNA fragment is bound to a solid support. Numerous solid supports to immobilize DNA are known in the art. Examples include, without limitation, streptavidin beads, which would bind to a PCR product labeled with biotin, and anti-digoxigenin beads, which would bind to a PCR product labeled with digoxigenin, and beads conjugated to nickel, which would bind to a six-histidine labeled product. In a preferred embodiment, streptavidin beads are used (FIG. 2).

Since the SARD tag position is dictated by the first restriction enzyme recognition site distal to the biotinylated primer used in the initial PCR reaction, there may be cases in which the first restriction enzyme recognition site is located within a conserved region of the gene of interest. In general, this will not be a problem because even though the tags from the conserved region may not be informative, most tags derived by SARD will be from a polymorphic region and will be informative. However, if one desires to decrease the number of tags that contain information from a conserved region of a gene rather than from a polymorphic region, one may purify the desired PCR products after restriction. In a preferred embodiment, one may do this by gel purifying those PCR products that have the expected size.

Step III. Digestion of the Amplification Product and Ligation to Linkers

The immobilized products are split into two pools and linkers are attached to the immobilized products of each pool. Each linker is a double-stranded synthetic DNA molecule comprising a specific DNA sequence. Both linkers incorporate a Type IIS restriction enzyme site. In a preferred embodiment, the two linkers incorporate the same Type IIS restriction enzyme site. Each of the two linkers also comprises a DNA sequence that specifically hybridizes to a primer. In one embodiment, the linkers are identical to one another and hybridize to the same primer. In a preferred embodiment, the linkers are different from each other such that each hybridizes to a different primer.

The double-stranded linker is ligated to the immobilized PCR product. The linker may incorporate the Type IIS restriction enzyme site or it may incorporate only a portion of the site. In this case, the linker will be designed such that ligation of the linker to the restricted DNA will reconstitute the Type IIS restriction site. In a preferred embodiment, the linker incorporates a BpmI site. Linker ligation is well-known and may be accomplished by any method known in the art. After ligation, the immobilized PCR product is isolated from the free linkers by any method known in the art. See, e.g., Velcelescu et al., Science 270: 484-487, 1995; Powell, Nucleic Acids Research 14: 3445-3446, 1998; Sambrook et al., pp. F.8-F.10, 1989.

Type IIS restriction enzymes cleave at a defined distance up to 20 basepairs away from their asymmetric recognition sites. Type IIS restriction enzymes that are commercially available include enzymes that leave 5' overhangs and those that leave 3' overhangs as double-stranded DNA products. Some enzymes of the former class include: BsmFI (10/14), Bst71I (8/12), and FokI (9/13), where the number in parentheses indicate the cleavage position on the same DNA strand as the recognition sequence/cleavage position on the complementary DNA strand. Enzymes of the latter class include: BpmI (16/14), BsgI (16/14), Eco57I (16/14) and GsuI (16/14). The 3' overhang left by these enzymes must be removed for a blunt ligation (Step IV). Therefore, enzymes that cleave at positions 16/14 result in a 14 base-pair tag. Other enzymes that cut at a more distal position could create a larger tag. For instance, MmeI (20/18) leaves a 3' overhang, but is not commercially available (Tucholski, J. et al., 1995, MmeI, a class-IIS restriction endonuclease: purification and characterization. Gene 157: 87-92).

Step IV. Digestion of the Product with Type IIS Restriction Enzyme

The product is digested with the appropriate Type IIS restriction enzyme to release a DNA fragment from the anchoring bead and produce a short hybrid DNA fragment containing a portion of the polymorphic region of the DNA of interest (the tag) and the linker DNA. After digestion, the DNA must be either filled in or digested to create blunt ends. If the Type IIS restriction enzyme produces a 3' overhang, the fragment is digested with T4 DNA polymerase to remove the 3' overhang. If the Type IIS restriction enzyme produces a 5' overhang, the overhang must be filled in using the appropriate deoxynucleotides and the Klenow fragment of DNA polymerase I. The DNA fragment is separated from the rest of the immobilized PCR product. In a preferred embodiment, the two pools of immobilized PCR products are digested with BpmI to release the polymorphic markers and digested with T4 DNA polymerase to create blunt ends (FIG. 2).

Step V. Ligation of Tags and PCR Amplification of Resulting Ditags

The tags are blunt-end ligated to one another using methods well-known in the art to form ditags. See, e.g., Sambrook et al., 1989; Velcelescu et al., Science 270: 484-487, 1995. The ditags are subsequently amplified by PCR using primers that are unique to the linkers used in Step III. In a preferred embodiment, the primers are different from one another if the linkers used in Step III were different from one another. Alternatively, the primers may be the same if the linkers used in Step III were identical to one another. The number of PCR amplification reactions will vary depending upon the amount of DNA present in the starting material. If there is a large amount of DNA, then only one PCR amplification reaction, wherein each reaction comprises from approximately 15-30 cycles, will be required at this step. If the starting amount of DNA is low, then more than one PCR amplification reaction may be required at this step.

Step VI. Cleavage of the Ditags and Ligation to Form Ditag Concatemers

The ditags are cleaved with the four-base restriction enzyme used in Step II. The products are then ligated to create ditag concatemers. In one embodiment, the ditag concatemers range from 2 to 200 ditags. In a more preferred embodiment, the concatemer comprises 20-50 polymorphic tags. The concatemer may be sequenced directly, or may be cloned into a sequencing vector. Using a 96-channel capillary DNA sequencer, about 12,000 tags. could be easily analyzed in one day. Alternatively, the concatemers may be sequenced manually.

Methods to Analyze Marker Data

Figure 8:
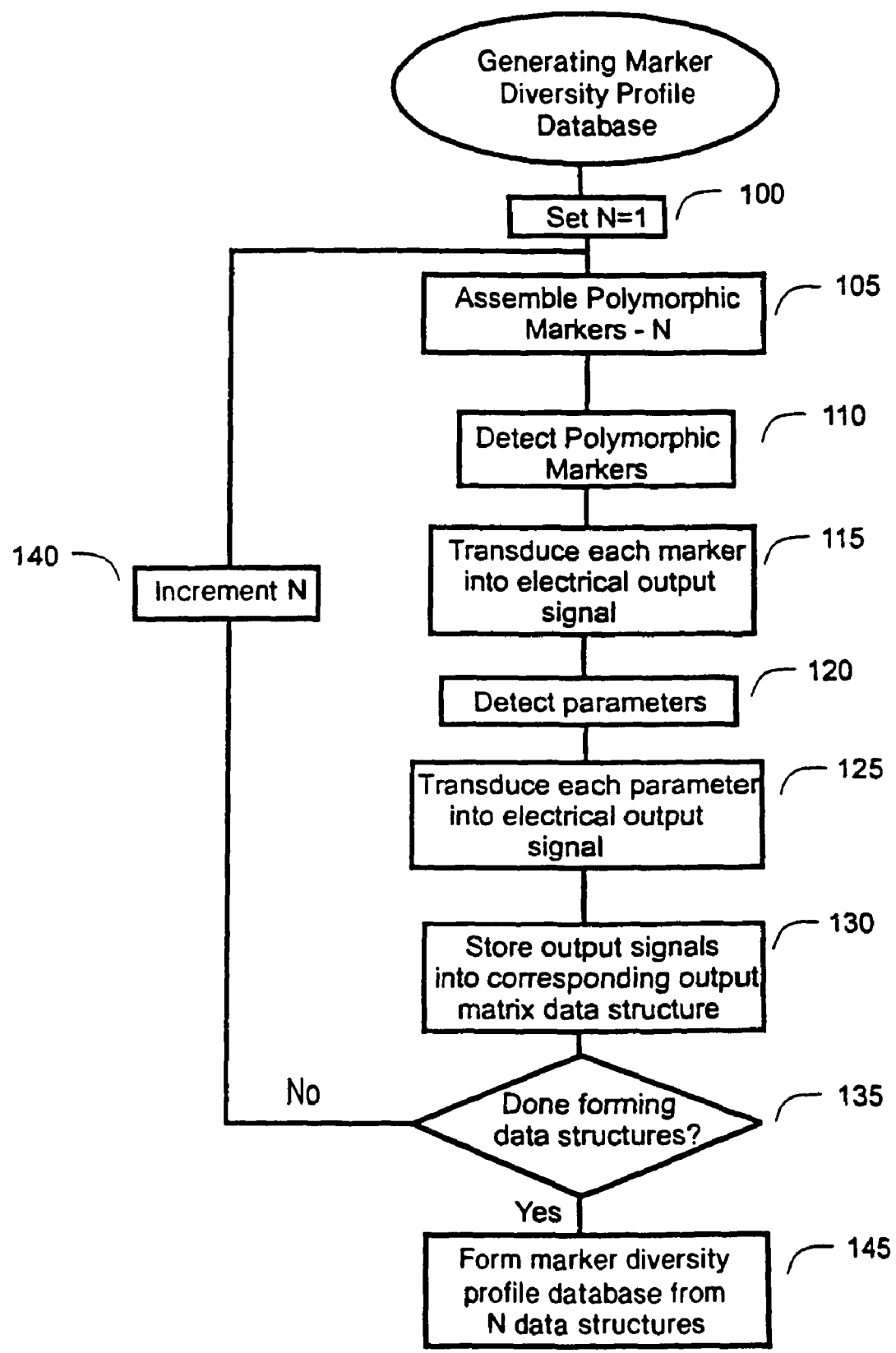
FIG. 8 shows a schematic for generating a marker diversity profile matrix database. The first step 100 involves assigning N an integer value of 1 corresponding to the first MDP data structure. The second step 105 involves assembling polymorphic markers from a sample. Examples of methods for assembling such markers are described in this application and include, but are not limited to, SARD (FIG. 2, Tables I and II) or mass tag compilation (Table III). The next step 110 involves detecting the polymorphic markers. Examples of methods to detect polymorphic markers described above include DNA sequence analysis of SARD tags and MALDI-TOF analysis of mass tags, respectively. This detection step includes detecting the presence and abundance of each marker in the sample. The next step 115 involves the conversion or transduction of the MDP into an electrical signal output. Generally, this process is a linear electronic conversion of the data into a digital signal. Step 120 involves detecting parameters that are associated with the sample N. Step 125 involves transducing the sample parameter data, which may include, without limitation, such parameters as pH, grain size, elemental analysis and/or organic analysis, into an electrical Signal output in the form of a digital signal. Step 130 involves storing into the memory of a computer the output signal from each MDP into a matrix data structure and associating it with sample parameters. The next step is a decision block 135 where if all the data structures have not been completed the routine advances to step 140 where n is incremented and the data structure generating steps 105-130 are repeated for the n +1$^{th}$ marker diversity profile. Once all the data structures are completed the routine proceed to step 145 to form the MDP database from n data structures. Each marker is assigned a unique identifier along with its relative abundance in the population. This information is also optionally indexed with other known parameters that are associated with the sample including, for instance, the time, date, elevation and geographical location. These signals are digitized and stored in the memory of a computer.

The invention is directed toward methods of analyzing the genetic diversity of a population in a sample. Each population that is analyzed will have its own unique set of different organisms or genes. The data set that is captured from each sample should recapitulate the genetic structure in a survey format to include a marker for each gene or organism and the relative abundance of each gene or organism in the population as a whole. The markers for a particular population form a marker diversity profiles (MDPs), that may be entered into a database. See, e.g., FIG. 8 which shows one schematic for generating such a database. The method by which the data are captured is not critical as long as it produces an accurate representation of each population.

In one aspect of the method, MDPs are entered into a database. In a preferred embodiment, the database is kept in a computer-readable form, such as on a diskette, on a non-removable disk, on a network server, or on the World Wide Web. However, the method by which the data are captured is not critical as long as it produces an accurate representation of each microbial community.

Artificial intelligence (AI) systems can perform many data management and analysis functions. Examples of AI systems include expert systems and neural networks. Expert systems analyze data according to a knowledge base in conjunction with a resident database. Neural networks are comprised of interconnected processing units that can interpret multiple input signals and generate a single output signal. AI systems are ideally suited for analyzing complex biological systems including populations through the use of deduction protocols.

Figure 9:
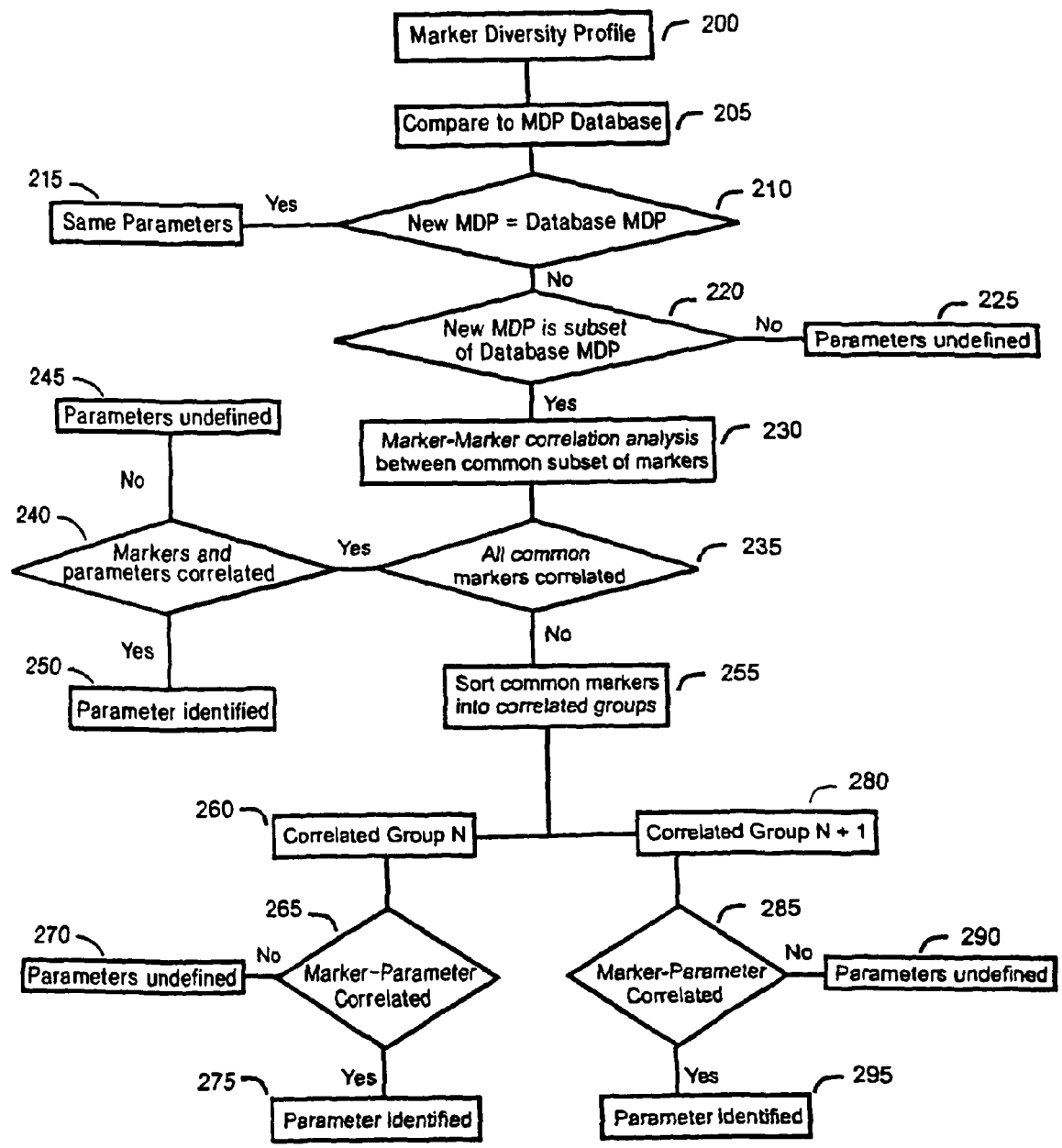
FIG. 9 shows a schematic of the steps involved in determining parameters associated with an MDP. A marker diversity profile 200 is created for a sample. The marker diversity profile is subject to a comparison function 205 which compares the profile with resident marker diversity profiles in the database. Step 210 is a decision block where a query is made whether the new marker diversity profile equals a resident marker diversity profile in the database. If the query returns a "Yes" the new marker diversity profile is deduced 215 to share the same, parameters as the resident marker diversity profile. Since the parameters associated with the resident marker diversity profile are characterized, the parameters associate with the new marker diversity profile are identified.

A marker may be correlated with a particular condition or with another marker. See, e.g., FIG. 9 for a schematic of the steps involved in determining particular parameters associated with an MDP and FIG. 10, which shows a schematic for generating a marker diversity matrix database. A condition or state may be an environmental condition such as pH, temperature, salinity, or the presence or absence of an organic or inorganic compound such as hydrocarbons, nitrates or mineral deposits. A condition may be a physiological or medical condition such as an acute or chronic disease state, physiological state, developmental stage or associated with a particular body tissue or fluid. Information regarding all known parameters associated with the samples will also be saved together with the MDPs.

Each MDP is composed of markers which represent a small number, more preferably one, species or gene. For instance, in the case of Example 1, each marker would be comprised of a 12 base-pair polymorphic 16S rDNA sequence. Such parameters that relate to environmental samples may include inorganic components (obtained through atomic adsorption analysis), organic components (obtained through GC-MS or LC-MS), grain size analysis, pH, and salinity. Parameters that relate to medical samples would include, but are not limited to, a complete medical history of the donor. See, e.g., FIG. 11, which shows a schematic for mapping applications using marker diversity profiles.

In another aspect of the invention, MIPs are collected for a time course, and each time point is one of the parameters included. Time courses may be useful for tracking changes over time for a wide variety of indication. For example, time courses may be useful for tracking the progression of a disease, during environmental remediation efforts, and during oilfield production.

In another aspect of the invention, MDPs are collected in various distinct locations, such as in various geographical locations or in various tissues of the body. Comparison of MDPs compiled from various distinct locations are useful for distinguishing changes between these various locations, which may be indicative of particular environmental conditions or disease states.

Comparison of marker diversity profiles can reveal trends in populations either relative to time or to geographical location. In the latter case, comparisons of microbial populations can resolve special information about the environment that would otherwise be undetected. Examples of such information include migration patterns of water, organic compounds and minerals. For instance, placer deposits of minerals are caused by the action of both water and wind causing the minerals to migrate from a lode deposit at one location only to deposited at another location. The migration of such minerals may leave a detectable trace upon the microbial populations in the path of migration. Physical attributes of the environment could also be detected such as structures, formations and fault lines. It is commonly understood that faults offer a significant vertical migration route for gases such as methane which is known to be differentially utilized by microbes. By combining MDP data with geographical coordinates such as elevation, longitude and latitude that can easily be obtained with global positioning system devices, it is possible to create maps delineating the distribution of various microbes in the environment.

Figure 5:
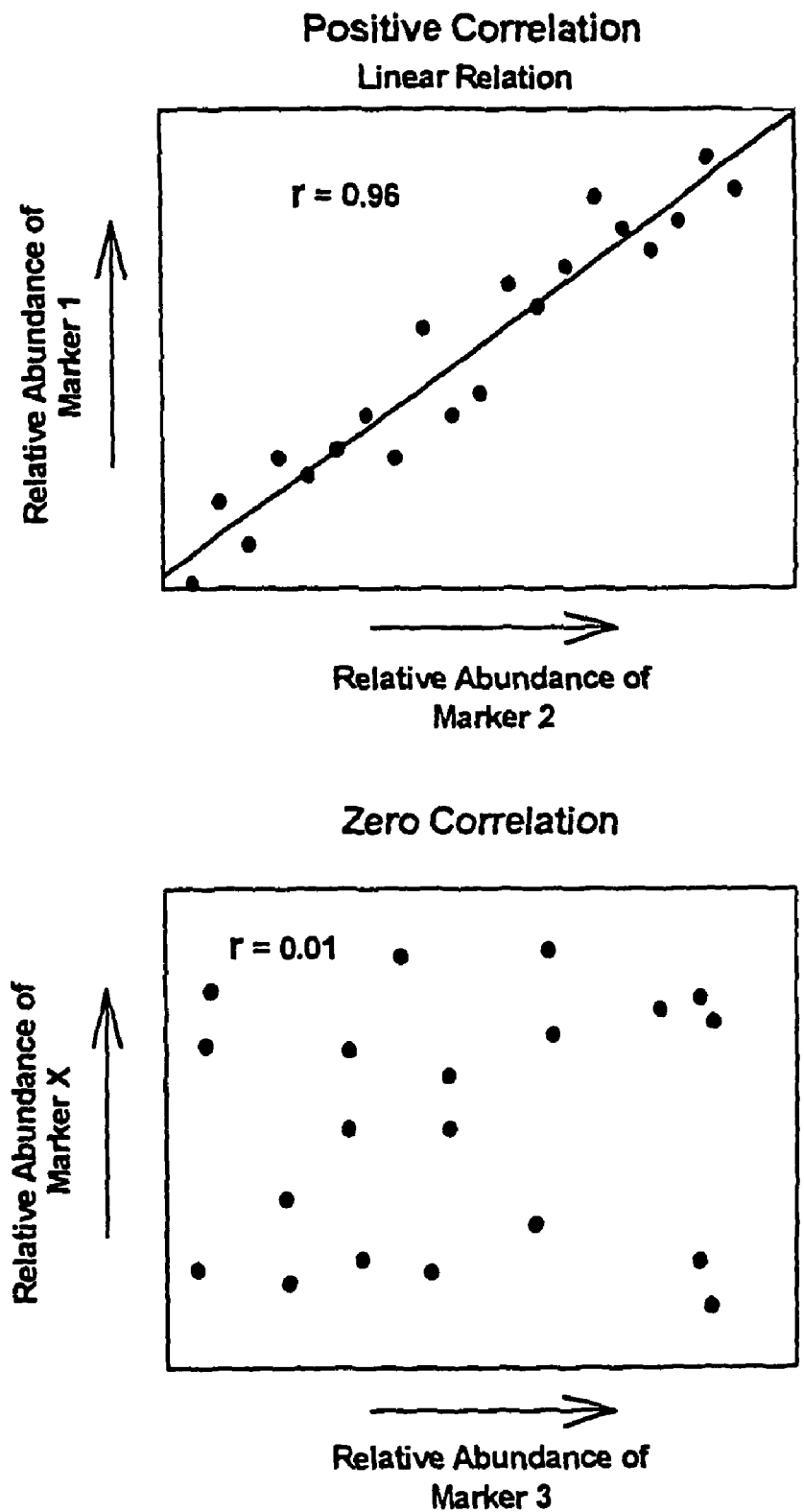
FIG. 5 shows examples of Marker-Marker correlation scatter plots. Each point represents a single sample population.

Correlation analyses between one marker and all the other markers in the database will reveal pairs of markers that have a propensity to coincide. This process can be repeated in an iterative manner for all markers to produce a matrix of correlation coefficients between all observed markers. FIG. 5 shows a scatter plot for two pairs of markers with one of the pairs exhibiting a high degree of correlation. This approach can also be used to create a dendrogram that reflects the relative level of correlation between each marker. Therefore, at any chosen level of correlation, all of the observed markers can be divided into groups where the markers in each group share the same level of correlation with each other member of the group. If a high correlation coefficient value is chosen (e.g. 0.8), the markers of each group would, more often than not, be found in the same sample. Thus, this exercise will divide a given population into groups of genes or organisms that have a propensity to co-localize with each other. In one preferred embodiment, the exercise will divide a microbial community into groups of microbes that have a propensity to co-localize.

Figure 6:
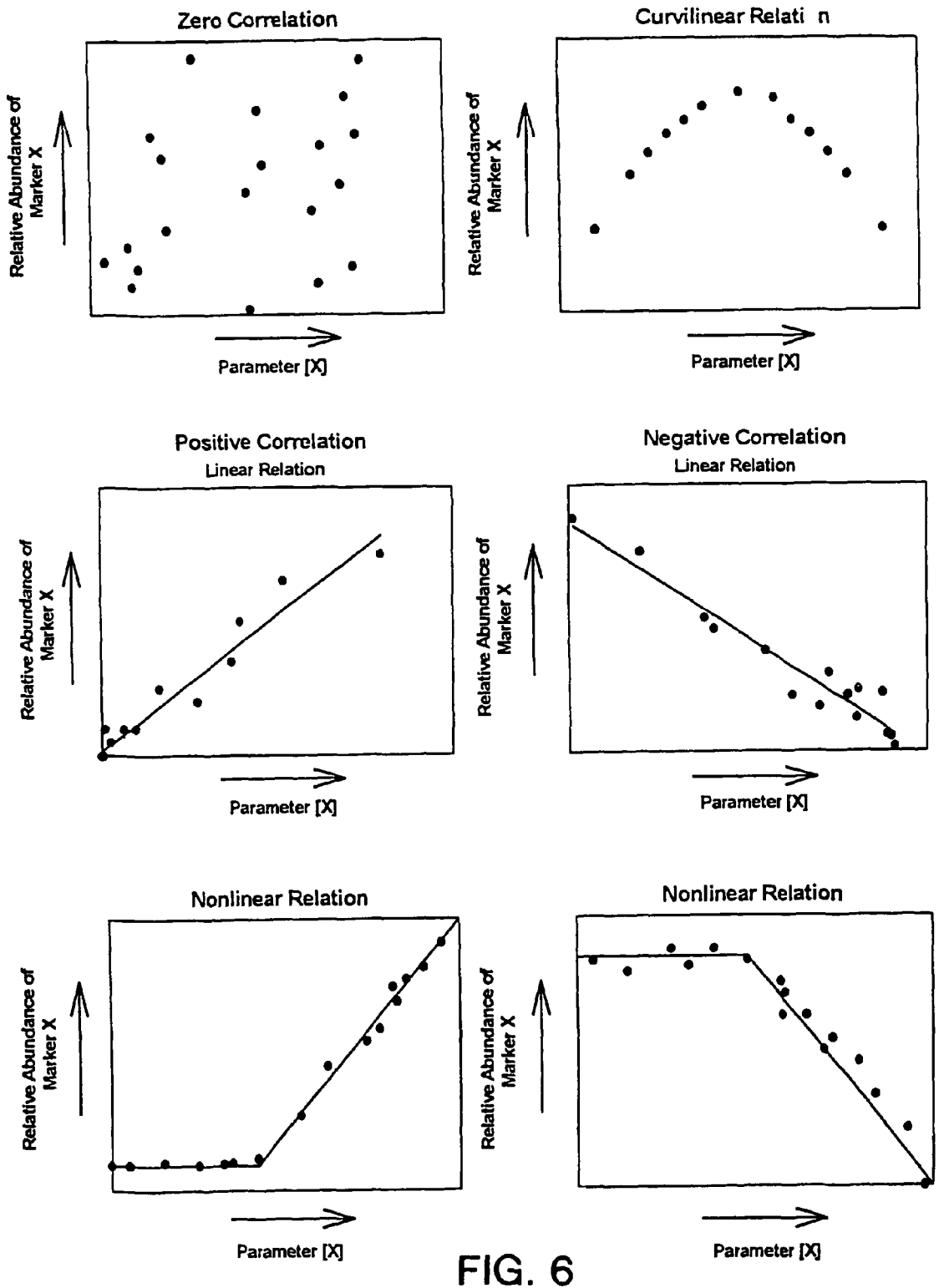
FIG. 6 shows examples of various Marker-Parameter scatter plots. Each point represents a single sample population.

Correlation analysis between a marker (variable 1) and a sample parameter (variable 2) will identify markers whose presence often, or invariably, coincides with a component present in the samples. Some types of relationships between markers and sample components (or parameters) are shown in FIG. 6. A strong correlation value between a marker and sample parameter would allow predictions to be made about the abundance of either variable (marker or sample parameter) as long as one of the variables is known.

In some cases, a marker will not be specific for a single species or gene. For example, the tag sequence that would be identified by the approach depicted in Example 1 would be identical for *Denitrobacter permanens* and *Legionella anisa*. In the cases where a significant correlation is found between a marker and sample parameter of interest, the preferred action is to use the tag sequence information to identify the complete gene sequence. The sequence can then be used to identify the species and to identify species-specific probes to verify the correlation. One may do this using methods known in the art, such as by PCR or by hybridization to DNA molecules isolated from the sample of interest, followed by sequencing or other method of analysis.

Species-specific probes that are identified from markers with a robust correlation to a sample parameter of interest can then be utilized as a diagnostic or to prospect for the parameter of interest. Such assays would preferably be PCR-based and would be highly sensitive, rapid and inexpensive. In a preferred embodiment, a marker identified by these methods may be used as a hybridization probe to identify a larger piece of the DNA from which the marker is derived. The sequence of the larger DNA molecule can then be used to design primers that will specifically hybridize to the DNA molecule of interest and which can be used to specifically amplify the DNA molecule by PCR. Alternatively, one may use a hybridization-based assay using a probe that binds specifically to the DNA molecule of interest. Using specific primers or probes are especially useful for quickly determining whether a large number of samples contains the DNA molecule that correlates to the parameter of interest.

In a preferred embodiment, a marker that correlates with a desired parameter is identified. The marker may be identified using SARD, or may be identified using another method, such as restriction fragment length polymorphisms (RFLP) or terminal restriction fragment length polymorphisms (T-RFLP; Liu et al., Applied and Environmental Microbiology 63: 4516-4522, 1997). A method such as denaturing gradient gel electrophoresis (DGGE) may be used to identify size differences. In a preferred embodiment, SARD is used to identify the marker. Other samples are screened to determine whether they have the marker of interest. In a preferred embodiment, the screen used is PCR or hybridization, more preferably PCR. In an even more preferred embodiment, the marker correlates with the presence of mineral deposits or petroleum reserves.

Figure 7A:
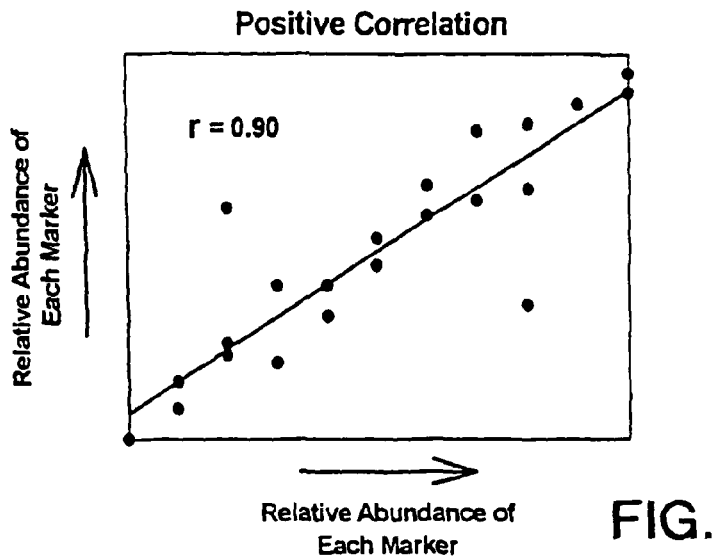
FIGS. 7A, 7B and 7C shows scatter plots comparing Marker Diversity Profile (MDP) profiles. Each point represents one marker.
Figure 7B:
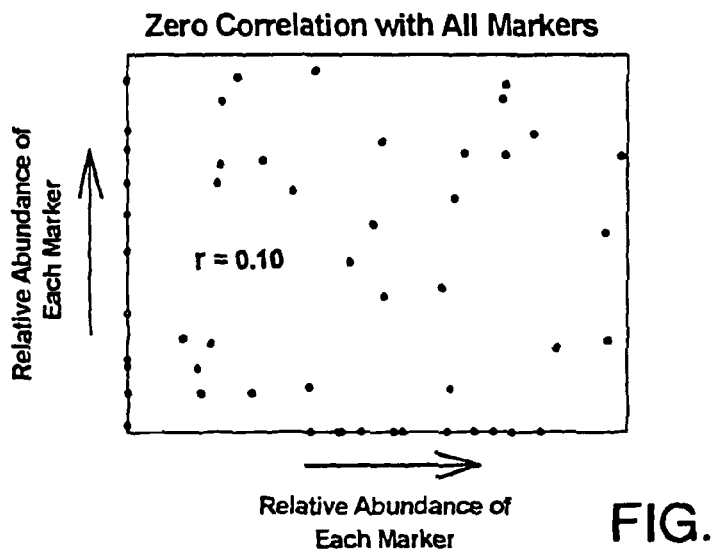
Figure 7C:
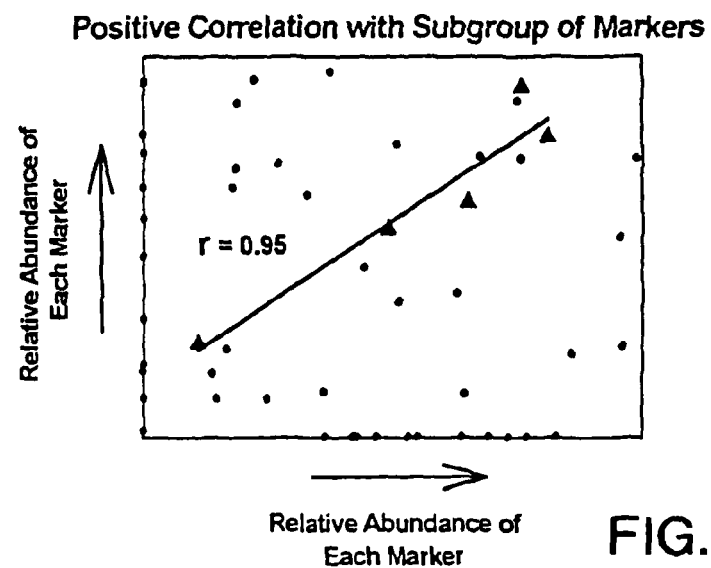

Correlation analysis between MDPs (MDPn, variable 1; MDPn+1, variable 2) can reveal the relative similarities between samples. Samples taken from the same individual or from proximal environmental sites that have similar composition, are expected to show a robust correlation coefficient (FIG. 7A). However, samples that share only one or a few parameters in common are expected not to show a significant correlation when all of the markers are considered (FIG. 7B). By incorporating the knowledge learned from the Marker-Marker and Marker-Parameter correlations, MDPs can be compared using either individual markers or preferably, subsets of correlated markers in the analysis (FIG. 7C). This approach can eliminate much of the noise and enable one to identify hidden relationships.

Correlation analyses may be performed by any method or calculation known in the art. Correlation analyses for r and $r^2$ may be performed as described by M. J. Schmidt in *Understanding and Using Statistics*, 1975 (D. C. Health and Company), pages 131-147. The degree of correlation for r may be defined as follows:

| | |
|---|---|
| 1.0 | Perfect |
| 0.8-0.99 | High |
| 0.5-0.7 | Moderate |
| 0.3-0.4 | Low |
| 0.1-0.2 | Negligible |

In one embodiment, the correlation between two markers or between a marker and a parameter is at least low (r is 0.3-0.4). In a preferred embodiment, the correlation is at least moderate (r is 0.5 to 0.7). In a more preferred embodiment, the correlation is high (r is 0.8 to 0.99).

With the development of numerous genomic technologies for analyzing complex sets of nucleic acids, we have the opportunity to begin to catalog the reservoir of microbial, and hence, metabolic diversity. Since the proliferation of a microbe in a given location will depend upon the presence of the requisite metabolic nutrients, information as to the abundance of that microbe can serve as a biosensor for a given set of parameters. When viewed as a whole, the microbial community structure in a given location will hold intrinsic biosensor potential for a wide range of parameters. The predictive reliability of the data from a complete microbial community will also be significantly increased. For example, if a given microbe were present in 50% of soil samples taken above petroleum reservoirs and were found nowhere else, then the presence of ten such microbes would create a predictive value with 99.9% accuracy.

Applications of the Invention

Geochemical and Mineral Exploration

The methods described in this invention have several benefits over existing technologies. For instance, in the area of geochemical exploration, genomic rDNA-based assays potentially will be able to resolve an extensive set of geochemical parameters of interest to the petroleum and mining industries. Currently, many different technologies are required to measure these parameters. Because this invention is based upon a universal measure, nucleic acid detection, it can greatly reduce instrumentation and sample outsourcing costs.

Oil and gas reservoirs are located well beneath the earth's surface at depths from a few hundred feet to more than 10,000 feet. When oil is formed, it undergoes a migration in which one of two things take place. The oil may continue to migrate until it ultimately reaches the surface, where it evaporates over time. Alternatively, its migration may be blocked by an impermeable structure, a so-called "trap". Geophysical methods (such as three-dimensional seismic methods) for petroleum exploration relies on finding these trap structures with the hope that they contain oil.

Crude oil is made up of a variety of hydrocarbon chain lengths. The lightest hydrocarbons (namely methane, ethane, propane and butane) are often able to diffuse through the trap structures and, as a result of pressure gradients, undergo a vertical migration to the surface. Certain microbes present at the surface or in the surface layer are able to utilize these migrating hydrocarbons, which occasionally results in mineralogical changes that are detectable at the surface. Thus, these migrating hydrocarbons would be expected to affect microbial populations, such that the ability to determine the genetic diversity of a microbial population may reveal microbial signatures that are indicative of the presence of oil.

Recent advances in microfluidics in the genomics industry have resulted in the development of instruments that can detect specific nucleic acids within a few minutes. Utilizing such instruments will enable measurements to be made in the field for a variety of parameters. In contrast, conventional chemical assays require laboratory analysis and interpretation.

Biosensors have been created that are able to detect hydrocarbons present at, or below, the level of detection of sophisticated GC-MS analytical instrumentation (Sticher, P. et al., 1997, Development and characterization of a whole-cell bioluminescent sensor for bioavailable middle-chain alkanes in contaminated groundwater samples. *Appl Environ Microbiol*. 63:4053-4060). Sticher et al. demonstrated that by using single reporter gene in a genetically engineered microbe comprising a reporter gene was able to sense extremely small changes in their environment in response to an acute treatment with a particular hydrocarbon. The instant invention could document the effect upon a population comprising thousands of microbes over geologic time and thus, has the potential of being more sensitive than current analytical instruments.

This invention may also be used to create a survey of biological entities that is limited only by the prerequisite that these entities contain nucleic acids that are arranged in regions that are conserved and regions that are polymorphic when compared to sequences from related organisms. Some additional examples of the application of this invention are described below.

Oil and Gas Reservoir Development

In addition to the application of this invention in petroleum exploration, this invention could also be useful in the development of oil and gas reservoirs. Several properties of oil reservoirs that directly affect the commercial viability of the reservoir are modulated at some level by microbes. Hydrogen sulfide is sometimes present in crude oil and can render otherwise 'sweet' oil into 'sour' oil. In addition to its corrosive effect on oilfield equipment, $H_2S$ also poses risk to the workers and significantly reduces the value of an oil reservoir since a washing plant must be installed to remove the gas. The levels of $H_2S$ can change during the development of a reservoir and is now thought to be the result of sulfate-reducing bacteria (Leu, J.-Y. et al., 1999, The same species of sulphate-reducing Desulfomicrobium occur in different oil field environments in the north sea. *Lett. Appl. Microbiol*. 29(4):246-252). By identifying the presence of microbes that could lead to $H_2S$ production, the valuation of new reservoirs and the resulting developmental strategies could be made more effective.

Crude oil and natural gas are composed of a complex mixture of hydrocarbons including straight chain hydrocarbons of lengths generally between 2-40 carbon atoms. The shorter chain-length hydrocarbons are more valuable (e.g. gasoline, $C_4$-$C_{10}$). In some oil reservoirs, the lighter hydrocarbons are selectively removed either during or prior to development of the reservoir. Microbes have been suspected to play a role in this process since the shorter chain-length hydrocarbons are more bioavailable. This invention could identify microbes that are involved in this process and therefore make predictions as to the susceptibility of certain reservoirs to the depletion of short chain hydrocarbons. This invention may also be able to identify microbes capable of shortening long chain hydrocarbons thereby increasing the value of existing reservoirs.

Insect and Parasite Detection

The significant negative impact insects can have on agriculture is widely known. Insects can also serve as vectors for the transmission of many disease causing microbes. Numerous microbe-insect relationships have been described. For example, the bacterial genus Wolbachia is found associated with many species of ants and has been shown to alter sex determination and fecundity in the host (Wenseleers, T. et al., 1998, Widespread occurrence of the micro-organism Wolbachia in ants. *Proc. R. Soc. Lond. B. Biol. Sci*. 265(1404):1447-52). In addition, many intracellular endosymbiotic bacterial species have been identified in ants (Schroder, D. et al., 1996, Intracellular endosymbiotic bacteria of Camponotus species (carpenter ants): systematics, evolution and ultrastructural characterization. *Mol. Microbiol*. 21:479-89). Most, if not all, insects probably have species-specific intimate relationships with microbes which could represent could represent an Achilles heel for the control of insect populations. The invention described in this application could provide a means to identify microbes that modulate the well-being of a given insect species.

The identification of microbes that are specifically associated with a given insect could also potentially serve as a the basis for a highly sensitive test for the presence of the insect. For instance, current methods to identify the presence of termites in wooden structures is based on visual inspection and is largely inadequate. A test for the presence of a termite-associated microbe that is based on PCR-amplification would be both non-invasive and highly sensitive.

Further, the ability to create comprehensive inventories of microbial diversity has several applications that relate to microbial ecology that would have utility in the agricultural industry. For instance, the agriculture industry utilizes enormous amounts of pesticides prophylactically to prevent loss of crops. This invention provides the ability to perform comprehensive surveys of microbial populations and could lead to predictions as to the susceptibility of a given field to particular plant pathogens. This knowledge could lead to a better strategy of pesticide applications.

Further, surveying microbial diversity in an environment such as a agricultural field at various times of the year would reveal the dynamic changes in microbial populations that occur as a result of seasonal fluctuations (temperature and moisture), pesticide application and the proliferation of certain organisms.

Comparison of the diversity profiles taken from the same or similar site at different times would reveal interactions between species in a population. These productive interactions may manifest themselves either in the increase or decrease in the representation of one marker relative to the decrease or increase in the representation of a second marker, respectively.

Such information could provide an early warning of the proliferation of a pest species as well as the identification of species that are pathogenic to a pest species. These pathogenic organisms may have value either as a biological agent to control proliferation of pest species and/or as a source for genes or compounds that would act as pesticides. This phenomenon is not be limited to microbe-microbe interactions. The eggs as well as larval stages of insects likely interact with soil microbes and create a detectable impact upon microbial populations. An example of such an organism is *Bacillus thuringensis*, which itself is commonly used in organic farming as an insecticidal agent. The gene responsible for this insecticidal activity (Bt toxin) has been widely used to create transgenic plants with resistance to insect attack.

Bioremediation

A considerable amount of effort has gone into the development of methods for microbe-based removal of chemicals from the environment. Such chemicals include heavy metals, polynuclear aromatics (PNAs), halogenated aromatics, crude oil, and a variety of other organic compounds such as MTBE. Regulatory considerations for the release of micro-organisms into the environment have re-directed efforts towards identifying and augmenting the growth of endemic organisms that have the capability to metabolize or remove compounds of interest from the environment.

The present invention can facilitate bioremediation efforts in two ways. First, organisms can be identified at a given site that have either been previously shown to be capable of removing compounds of interest, or that have significant likelihood of having the capacity metabolize the relevant compounds based upon its coincidence in the environment with the chemical in numerous geological settings. Secondly, this invention can identify trends of soil types and particular microbial species. In this case, the correlations that are drawn from the database between microbial distribution and soil types can be coupled with the existing knowledge base of geochemistry. For instance, the USGS provides many publically available maps describing numerous geochemical and geophysical parameters. Extrapolations of the distribution of microbial species can be made to the regional, and possibly worldwide, level. These extrapolated microbial distributions could serve as the basis for site-specific treatment regimens to augment the growth of certain relevant species without first performing a microbial survey.

Immunological Applications

Methods could be applied to map immunoglobulin and TCR gene rearrangements which occur normally during B and T cell differentiation. These rearrangements could provide a profile of an individual's immunoglobulin and TCR diversity that could be correlated with medical history. This type of analysis might lead to the early diagnosis of certain conditions or diseases and allow for a more proactive and early treatment. Further, samples of immune cells could be isolated from individuals or certain body fluids or tissues to identify potential immunoglobulin or TCR profiles that may be correlated with particular diseases, particularly autoimmune diseases. For instance, it has been demonstrated that T cells expressing particular TCR subtypes are found in higher levels in the synovial fluid of individuals suffering from rheumatoid arthritis. The methods of the instant invention may be used to identify other correlative immunoglobulin or TCR profiles in autoimmune and other diseases.

Virus Detection

The human genome contains thousands of copies of human endogenous retroviruses (HERVs) that make up as many as 1% of the human genome (Sverdlov, E. D. 1998, Perpetually mobile footprints of ancient infections in human genome. *FEBS Lett.* 428:1-6). These sequences are thought to be remnants of infections that occurred millions of years ago. These sequences can transpose to other locations in the human genome and may be responsible for disease-susceptibility in certain human populations (Dawkins, R. et al., 1999, Genomics of the major histocompatibility complex: haplotypes, duplication, retroviruses and disease. *Immunol. Rev.* 167: 275-304). This invention could be used to survey HERV polymorphic sequences and determine whether they correlate with a variety of clinical parameters.

Forensic Science

This invention, particularly SARD analysis, can be-used in forensic applications as well. Studies over the past ten to twenty years have focused upon the changes that occur in a person's or animal's body after death. Many of these changes involve changes in microbial populations that occur during decomposition of the body. Changes in microbial populations have been correlated with length of time that a person has been dead and the conditions that the body experienced after death, e.g., heat, sun exposure, partial or complete burial, rain, etc. SARD analyses would permit forensic scientists to quickly and accurately determine the size and type of microbial populations, which in turn may be used to determine more accurate times of death as well as conditions that the body may have been exposed to.

Other Applications

This approach can be utilized for any polymorphic region in a genome, whether microbial, viral or eukaryotic that is flanked by conserved DNA sequences. This method also need not be restricted to genes. The DNA sequence of intergenic regions of genomes are not under as high a level.of selective pressure and thus, represent highly polymorphic DNA sequence. One example of such a region is the intergenic region between the large (23S) and small (16S) rDNA subunits coding regions. The above-described methods may be used to distinguish members of a population based upon size differences of the intergenic region between the 16S-23S-5S rDNA genes. The spacer region between these genes has been found to be hypervariable in. microbial populations. In the case of the 16S-23S intergenic region, the spacer size ranges between about 200-1500 base-pairs depending the, presence or absence of various tRNA,genes. (Nour M. 1998, .16S-23S and 23S-5S intergenic spacer regions of lactobacilli: nucleotide sequence, secondary structure and comparative analysis, Res Microbiol. 149(6):433-448; Berthier F. et al, 1998, Rapid species identification within two groups of closely related lactobacilli using PCR primers that target the 16S/23S rRNA spacer region, FEMS Microbiol Lett. 161(1):97-106; Tilsala-Timisjarvi A. et al., 1997, Development of oligonucleotide primers from the 16S-23S rRNA intergenic sequences for identifying different dairy and propionic lactic acid bacteria by PCR Int. J Food Microbiol 35(1):49-56). Both .of these rDNA genes are transcribed on the same operon. Therefore, the conserved regions of the rDNA coding sequence of these subunits can be utilized to amplify the intergenic regions.

In order that this invention may be better understood, the following examples are set forth. These examples are for purposes of illustration only and are not to be construed as limiting the scope of the invention in any manner.

EXAMPLE 1

Serial Analysis of rDNA Polymorphic Tags from the Domain Eubacteria

A sample comprising environmental bacteria was obtained and total DNA was extracted from the sample. To amplify the DNA, PCR was performed by mixing 5 μL 10×Advantage2 reaction buffer (Clontech), 2.5 μL dNTPs, 5 μL 8 μM TX9/TX16 primers, 50 ng of sample DNA, 0.5 μL Advantage2 Taq polymerase (Clontech) and water to 50 μL. Primer TX9 was biotinylated. The primers are shown in FIG. 12 and a general strategy of this example is shown in FIG. 13. The reaction mixture was then subjected to PCR under the following conditions:
 a) 94° C. for 5 minutes;
 b) 94° C. for 1 minute, 10 seconds;
 c) 55° C. for 50 seconds;
 d) 68° C. for 1 minute;
 e) repeat steps (b) through (d) 20 times; and
 f) 68° C. for 2 minutes.

The approximately 600 basepair PCR product was gel purified using 1% agarose and a Qiaquick kit (Qiagen) according to manufacturer's instructions. The DNA was eluted with 50 μL Tris-EDTA (TE; 10 mM Tris pH 8; 1 mM EDTA). To restrict the amplified DNA, 10×New England Biolabs Buffer #2 (NEB#2) was added to bring the concentration of the buffer to 1× and 25 units of AluI was added. The reaction mixture was incubated for 2 hours it 37° C.; 25 additional units of AluI was added and the reaction mixture was incubated for a further one hour followed by inactivation of the enzyme at 65° C. for 20 minutes.

In order to immobilize the restricted DNA fragment to a bead, an equal volume of 2×BW buffet (2×BW=10 mM Tris pH 7.5; 1 mM EDTA; 2 M NaCl) was added to the reaction mixture, followed by addition of 50 μL washed M-280 Streptavidin (SA) beads (Dynal). The reaction mixture was incubated for 20 minutes at room temperature. The beads were then washed twice in 1×BW and twice in wash buffer (10 mM Tris pH 8; 10 mM MgSO$_4$; 50 mM NaCl). During the last wash step, the beads were split into two pools.

To add the linkers to the immobilized DNA; one pool of beads were resuspended in 4 μL of 10 μM linker TX-12/13 (a double-stranded DNA molecule comprising primers TX-012 and TX-013) to form pool A, while the other pool (pool B) were resuspended in 4 μL of 10 μM linker TX-14/15 (a double-stranded DNA molecule comprising primers TX-014 and TX-015) was added to the other pool. 36 μL of T4 ligase mix (4 μL 10× ligase buffer; 32 μL water; 0.2 μL T4 ligase [400 U]) were added to the linker/bead mixture and the mixture was incubated overnight at 16° C.

The DNA molecule attached to the streptavidin beads was then incubated with BpmI, which recognizes its specific restriction sequence (GAGGTC) in the DNA molecule. BpmI cleaves the DNA such that it releases the streptavidin bead from the DNA molecule and incorporates a part of the polymorphic region of the DNA molecule first amplified. The beads were washed twice with 0.5 mL each 1× BW and twice with wash buffer. The beads were resuspended in 10 μL BpmI mix (1 μL 10× NEB#3 [New England Biolabs]; 1 μL 1 μg/μL bovine serum albumin; 8 μL water and 1 μL BpmI [New England Biolabs]). The reaction mixture was incubated at 37° C. for 2 hours and then at 65° C. to inactivate the enzyme. The supernatant containing the DNA tags was then isolated.

In order to remove the 3' overhang on the DNA tags and make them blunt ended, to the supernatant (10 μL) on ice was added 10 μL T4 polymerase mix (1 μL 10× NEB#2; 0.5 μL 4 mM dNTPs; 8.5 μL water and 0.33 μL T4 polymerase [1 U; New England Biolabs]). The reaction was incubated at 12° C. for 20 minutes and at 65° C. for 20 minutes to inactivate the polymerase. In order to form ditags, pool A and pool B were recombined to give a total volume of 40 μL. Four μL 10 mM rATP and 0.2 μL T4 DNA ligase (400 U) was added and the reaction was incubated 4 hours to overnight at 16° C.

As an intermediate amplification step, the ditags were then amplified in a 300 μL PCR reaction (30 μL 10× Advantage2 Taq buffer; 15 μL 4 mM dNTPs; 30 μL 8 μM TX111/TX121 primer mix; 3 μL Advantage2 Taq polymerase; 3 μL ditag template; 219 μL water). The 300 μL reaction mix was split into three 100 μL reactions and amplified using the following conditions:
 a) 94° C. for 5 minutes;
 b) 94° C. for 30 seconds;
 c) 56° C. for 30 seconds;
 d) 68° C. for 40 seconds;
 e) repeat steps (b) through (d) for 15 cycles; and
 f) 68° for 2 minutes.

After amplification, three volumes (900 μL) QG buffer (Qiagen) and one volume (300 μL) isopropanol was added, the mixture was bound to a Gel Extraction Spin Column (Qiagen) and the DNA was eluted with 50 μL TE.

The amplified DNA was then subjected to non-denaturing polyacrylamide gel electrophoresis (PAGE; Novex 1 mm 10% TBS-PAGE gel). The gel was stained with 5 μg/mL ethidium bromide, the approximately 106 basepair ditags were excised from the gel, the excised gel was fragmented and 0.3 mL of TE was added to the gel and incubated at 65° C. for 30 minutes. The gel/TE mixture was transferred to a miniprep spin column (Qiagen) and the eluate containing the amplified ditags was collected (the ditag template). This amplified DNA was called the P300 ditag template.

In order to determine the optimal number of PCR cycles for large-scale amplification (PCR cycle titration), 6.4 μL P300 ditag template was mixed with 8 μL 10×Advantage2 Taq buffer, 4 μL 4 mM dNTPS, 8 μL TX111/TX121 primers, 0.8 μL Advantage2 Taq polymerase and 52.8 μL water. The reaction mixture was split into three 25 μL reactions and amplified for 6, 8 or 10 cycles using the PCR conditions described above for the intermediate amplification step. After amplification, the DNA products were desalted and purified using a Qiagen Gel Extraction Spin Column as described above except that only 75 μL QG buffer and 25 μL isopropanol were used, and the DNA products were eluted with 20 μL TE. The cycle number that produced the largest 106 basepair ditag yield without any detectable vertical smearing by 10% TBS-PAGE analysis was used for large-scale amplification.

For large-scale ditag amplification, 180 μL 10×Advantage2 Taq buffer, 90 μL 4mM dNTPs, 180 μL 8 mM TX111/TX121 mixture, 18 μL Advantage2 Taq polymerase, 144 μL P300 ditag template and 1188 μL water was mixed together and then split into 18 100 μL reactions. PCR was performed as described immediately above using the number of cycles that were determined from the previous titration step. The PCR reactions were desalted by adding three volumes QG buffer and one volume isopropanol to the reactions and passed through a total of four Qiagen Gel Extraction Spin Columns. Each column was eluted with 50 µL TE. The samples were subjected to non-denaturing preparative PAGE (Novex 1.5 mm 10% TBS-PAGE). The-DNA bands were stained and excised as above and split into three tubes. The polyacrylamide was fragmented and eluted using TE as described above and the DNA was purified by passing the contents of the gel/TE mixture through a Qiagen Plasmid Spin Miniprep column as described above.

To precipitate the DNA, 1 µL glycogen, 150 µL 10M ammonium acetate and 1125 µL ethanol was added to each eluate of approximately 300 µL. The mixture was incubated at −80° C. for 20 minutes and microfuged at 13,000 rpm at 4° C. for 15 minutes. The pellet was washed with 1 mL 70% ethanol and dried at 37° C. for 5 minutes.

The DNA pellets were resuspended in 150 µL AluI mix (15 µL NEB#2, 135 µL water and 15 µL AluI [150 U]). The reaction mixture was incubated at 37° C. for 2 hours. 150 µL of 2× BW buffer was added and the sample was transferred to a new tube containing 150 packed SA beads. The beads were incubated with the DNA mixture for 30 minutes at room temperature and the beads were pelleted magnetically. The supernatant was removed, extracted with 250 µL phenol/chloroform/isoamyl alcohol, and the aqueous phase was precipitated with 150 µL 10M ammonium acetate and 1125 µL ethanol overnight at −80° C. The DNA was centrifuged at 13,000 rpm at 4° C. for 15 minutes, the pellet washed with 70% ethanol and dried. This step removes any free linkers that were present as well as any incompletely digested DNA products that were still bound to the biotinylated linkers.

In order to concatenate the ditags, the DNA pellet was resuspended in 10 µL ligase mix (1 µL 10× ligase buffer; 9 µL water and 1 µL T4 ligase [100 U]) and incubated at 16° C. for 30 minutes. The DNA was precipitated by added 40 µL TE, 25 µL 10M ammonium acetate and 180 µL ethanol. The DNA was precipitated for 15 minutes at −80° C. and centrifuged, washed and dried as described above.

The concatenated ditags. were purified by resuspending the pellet in 1× TBE loading buffer and subjecting the sample to non-denaturing PAGE (8% TBE-PAGE). The area between 0.5 to 1.2 kb was excised and the DNA was eluted from the gel into 300 µL TE as described above. The DNA was precipitated using 1 µL glycogen, 150 µL 10M ammonium acetate and 1125 µL ethanol. The DNA was precipitated, centrifuged, washed and dried as before.

The concatenated ditags were cloned in pUC19 by resuspending the DNA pellet in 3 µL SmaI-cut pUC 19(approximately 100 ng plasmid DNA) and adding 7 µL T4 ligase mix (1 µL 10× ligase buffer, 6 µL water and 0.2 µL T4 ligase [400 U]). The plasmid/ditag mixture was incubated for 2 hours at 16° C. and 1 µL of the mixture was used to transform 100 µL chemically-competent DH10B. Amp-resistant transformants were screened by PCR using pUC/m13 forward/reverse 17 mers as PCR primers. Transformants containing concatemerized ditags were then sequenced.

EXAMPLE 2

SARD Analysis of a Defined Population

SARD was performed essentially as described in Example 1. In this example, commercially available bacterial genomic DNA samples were mixed at an equal concentration (weight/volume). The bacterial DNA samples used included *Bacillus subtilis, Clostridium perfringens, Escherchia coli, Lactococcus lactis* and *Streptomyces coelicolor*. Equal volumes of the DNA samples (total genomic DNA) were mixed at a concentration of 50 ng/µL each. Chart I shows the size of the genomes of each bacterial species, the number of 16S rDNA copies per genome and the molar percentage of 16S copies for each bacterial species in the total DNA sample.

Chart I

| Bacteria | Genome (Mb) | 16S Copies/Genome | Molar % |
|---|---|---|---|
| B. subtilis | 4.2 | 10 | 17.2 |
| C. perfringens | 4.4 | 10 | 16.4 |
| E. coli | 4.6 | 7 | 11.0 |
| L. lactis | 2.4 | 10 | 30.7 |
| S. coelicolor | 8.0 | 6 | 5.4 |

After SARD, 120 tags were sequenced. Chart II shows the expected number and percentage of tags compared to the observed number and percentage of tags for the population. See also FIG. 14.

Chart II

| Bacteria | Expected Tag Number | Observed Tag Number | Expected Tag Percentage | Observed Tag Percentage |
|---|---|---|---|---|
| B. subtilis | 21 | 44 | 17.2% | 36.7% |
| C. perfringens | 20 | 18 | 16.4% | 15.0% |
| E. coli | 13 | 8 | 11.0% | 6.7% |
| L. lactis | 37 | 35 | 30.7% | 29.2% |
| S. coelicolor | 6 | 6 | 5.4% | 5.0% |

Each of the rDNA genes from these species produced a SARD tag that was distinguishable from the other members of the set. As can be observed, approximately twice as many tags that corresponded to 16S rDNA from *B. subtilis* were found than was expected based upon the molar percentage of 1 6S rDNA from *B. subtilis*. The observation that *B. subtilis* appeared to be twice as abundant as was expected has been reported previously. Farrelly et al. (Farrelly, V. F. et al., 1995, Effect of genome size and rrn gene copy number on PCR amplification of 16S rRNA genes from a mixture of bacterial species. Appl. Environ. Microbiol. 61(7):2798-2801) described similar results when PCR amplifying the 16S rDNA gene from mixed populations of genomic DNA. They concluded that this phenomenon was the result of the tandem organization fo the rrn operons in the *B. subtilis* genome where multiple rDNA genes may be amplified as a single product. The remaining tags were found at abundances close (<40% deviation) to their expected values.

EXAMPLE 3

SARD Analysis of Environmental Bacterial Diversity

In order to demonstrate that the SARD method could be used to survey environmental bacterial diversity, total DNA was extracted from two soil samples (Wy-1 and Wy-2) taken from the Rocky Mountain Oilfield Testing Center (RMOTC, Casper, Wyo.) in October, 2000. The samples were collected about 0.5 miles apart and from a depth of 14-18 inches. The environmental DNA samples were subjected to SARD analysis as described in Example 1. In a preliminary analysis, 148 tags were identified from Wy-1 and 234 tags were identified.fromr Wy-2 (FIGS. 15 and 16, respectively).

In the Wy-1 sample, 58 distinct tags were identified and the abundance of each tag varied. The most abundant tag (ATG-GCTGTCGTCAGCT) (SEQ ID NO: 6) made up about 34% of the population. This tag sequence is identical to many bacterial sequences in GenBank and its position within the 16S rDNA gene indicates that it is located in a conserved region located distal to the targeted AluI restriction site. In other words, the contributing 16S gene(s) for this tag did not contain the conserved AluI site. Since the SARD tag position is dictated by the first AluI site distal to the biotinylated primer used in the initial PCR reaction, it is likely that the first AluI site in the contributing 16S gene(s) was located downstream within a conserved region. In order to decrease the number of tags that do not contain the conserved AluI site next to the polymorphic region, one may gel purify the approximately 100 basepair PCR products after the first AluI restriction step. However, this may result in losing some information. Nevertheless, 39% of the tags (58/148) in this set were different from each other. See FIGS. 15 and 17.

The Wy-2 sample was found to contain 79 different tags out of a total of 234 tags that were examined. Thus, 34% of the tags (79/234) in this set were different from each other. See FIGS. 16 and 17. As in the case with Wy-1, the tag ATGGCT-GTCGTCAGCT (SEQ ID NO: 6), which represents a conserved sequence in a 16S rDNA gene, was most abundant and made up about 30% of the population.

Combining the tags from the two sets reveals a total of 105 different tags from a total of 382 tags. Thus, 26 of 58 different tags (45%) in Wy-1 were not present in Wy-2. Likewise, 47 of 79 different tags (59%) in Wy-2 were not present in Wy-1. The tags that were only found in one of the samples are candidates for bacteria with indicator value for various parameters associated with each sample. However, there was no attempt in this preliminary analysis to obtain all of the tags present in the two samples, so it cannot be concluded that some or most of the tags found in one sample are not present in the other sample. Thus, one cannot conclude that there are tags in these two samples that are indicators for various parameters associated with each sample. Nonetheless; a full-fledged analysis of these samples may provide such indicators.

EXAMPLE 4

Serial Analysis of rDNA Polymorphic Tags from the Domain Archaea

The method described in Example 1 can also be applied to the domain Archaea. The domain Archaea is made up of two known kingdoms, Euryarchaeota and Crenarchaeota (Pace, N. R. 1997, A molecular view of microbial diversity and the biosphere. *Science* 276:734-740). One set of oligonucleotides and restriction enzymes can be used to survey both of these domains.

In this example, the following oligonucleotides are designed: 5' biotin -TA(CT)T(CT)CCCA(GA)GCGG(CT)(GCT)(GC)(GA)CTT(AGCT)-3' (SEQ ID NO: 155) corresponding to position 817-838 of the *Methanococcus jannaschii* 16S rDNA gene (GenBank Accession number M59126), and (5'-GGTG(TGC)CA(GC)C(CA) GCCGCG-GTAA(TC)ACC(AGCT)-3' (SEQ ID NO: 156) corresponding to position 457-481 of the *Methanococcus jannaschii* 16S rDNA gene.

In this example, a BfaI site (CTAG) is utilized that corresponds to position 768-771 of the *Methanococcus jannaschii* 16S rDNA gene. This site is immediately flanking a polymorphic region.

The SARD method was tested in silico using 17 representatives from the domain Archaea (FIG. 4). 15 of the SARD tags that would be identified were all unique to this set (Table II). Two species of the genus *Methanobacterium* did not possess any BfaI sites in the region that would be amplified and therefore, would not produce any tags.

EXAMPLE 5

Surveying PCR-Amplified Polymorphic rDNA Regions

Oligonucleotide primers that are complementary to conserved regions immediately flanking a polymorphic region could be used to amplify the polymorphic DNA sequences. The oligonucleotide primer sequences could include existing or introduced restriction sites to enable subsequence cloning into a bacterial vector. By utilizing or introducing different restriction sites in each primer, the restriction digested PCR products could be concatemerized in a unidirectional fashion prior to cloning. This step would allow a serial sequence analysis of multiple polymorphic regions from a single recombinant product.

EXAMPLE 6

Surveying Translation Products of 16S rDNA Polymorphic Regions

The polymorphic regions of 16S rDNA could also be surveyed by the parallel identification of the translation products of a given polymorphic region. Oligonucleotides could be designed such that they can serve to amplify a polymorphic region. The 5' primer would also include a T7 polymerase binding site or other polymerase binding site, a Kozak consensus sequence, an initiator ATG codon and an epitope to facilitate purification. Examples of epitopes include hemagglutinin (HA), myc, Flag or polyhistidine. Following amplification, the products are subjected to in vitro transcription/translation to produce the peptide products. These peptides are purified from the cell extract and analyzed by mass spectrometry. This type of an approach has been applied to the identification of mutations in the BRCA1 gene(Garvin,A. M. et al., 2000 MALDI-TOF based mutation detection using tagged in vitro synthesized peptides. *Nature Biotechnol.* 18:95-97).

Although this process would not readily provide DNA sequence information from which to deduce taxonomy, it would allow for the creation of microbial diversity profiles comprised-of 'mass tags'. These mass tags could be used to identify correlations between specific tags and various sample parameters. To test the information content of this approach, a polymorphic region of the 16S rDNA genes from the species in FIG. 3 was translated in silico, Of the 34 polymorphic regions examined, 32 produced a tag with a unique mass in this set (Table III).

Another approach to translating the amplified polymorphic regions would be to clone and express the sequences in whole cells. For instance, oligonucleotides could be designed to amplify polymorphic regions that include sequences at the 5' ends that would allow for cloning by homologous recombination in yeast. These sequences could be cloned into an expression cassette to create a fusion between a secreted protein, such as alpha factor or invertase, and an epitope to facilitate purification and the translated amino acid sequence of the rDNA polyrmophic region. Homologous recombination in yeast is quite robust and could easily enable the isolation of $10^3$-$10^4$ independent recombinants on a single transformation plate. The secreted products could be isolated from the medium and identified by mass spectrometry.

EXAMPLE 7

Hybridization of Microbial rDNA to Immobilized Oligonucleotides

A complication with using short oligonucleotide, probes in DNA microarrays is the instability of short oligonucleotides duplexes. A possible solution to this problem is to synthesize probes that include degenerate sequences to accommodate unknown sequences. The length of the oligonucleotide is dictated by the number of degeneracies, or sequence permutations, that are to be accommodated. For instance, a fully degenerate 9 mer oligonucleotide requires $4^9$ or 262,144 different oligonucleotide sequences. The efficient hybridization of 9 mer oligonucleotides is not possible using standard conditions. One solution has been to incorporate a ligation step in the hybridization of a target sequence to a 9 mer oligonucleotide probe (Gunderson, K. L. et al., 1998, Mutation detection by ligation to complete n-mer DNA arrays. *Genome Res.* 8:1142-1153).

Another solution could be to effectively increase the length of the oligonucleotide by including nucleotides in the primer that are not degenerate. This approach could be applied to a survey of a microbial community by constructing oligonucleotide probes that are composed of a constant region that corresponds to a well conserved region of a 16S rDNA gene together with a degenerate sequence that corresponds to the flanking polymorphic region.

An example of such a collection of degenerate oligonucleotides for the domain Bacteria could include permutations of the following primer: 5'- AACGAGCGCAAC-CNNNNNNNNN-3' (SEQ ID NO: 157), where N indicates any nucleotide at that position. This sequence corresponds to position 1101-1122 of the *E. coli* 16S rDNA gene (GenBank Accession number E05133). Alternatively, the primers could be designed such that they are composed of a mixture of constant sequence, semi-degenerate positions (e.g. A or G) and degenerate positions (e.g. A, G, C or T).

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

TABLE I*

| Species | GenBank Acc# | Tag Sequence | Position | SEQ ID NO: |
| --- | --- | --- | --- | --- |
| *Desulfurobacterium thermolithotrophum*A | J001049 | GTCAGTTGCCGAAGCT | 814-829 | 158 |
| Uncultured *Aquificales* OPS132 | AF027104 | GTCCGTGCCGTAAGCT | 810-825 | 159 |
| *Bacteroides caccae* | X83951 | ATGGTTGTCGTCAGCT | 1021-1036 | 160 |
| *Actinomyces bovis* | X81061 | TTTCCGCGCCGTAGCT | 834-849 | 161 |
| *Actinomyces meyeri* | X82451 | TTTCTGCGCGTAGCT | 828-843 | 162 |
| *Denitrobacterium detoxificans* | AF079507 | CCTCCGCGCCGCAGCT | 788-803 | 163 |
| Uncultured GNS bacteria BPC110 | AF154084 | CCCGGTAGTCCTAGCT | 765-780 | 164 |
| Uncultured GNS bacteria GCA004 | AF154104 | CATCGGTGCCGCAGCT | 824-839 | 165 |
| Uncultured GNS bacteria GCA112 | AF154100 | CGGCGGTGCCGTAGCT | 826-841 | 166 |
| *Acetobacter aceti* | AF127399 | ACTCAGTGTCGTAGCT | 782-797 | 167 |
| *Gluconobacter asaii* | AB024492 | ACTCAGTGTCGAAGCT | 783-798 | 168 |
| *Burkholderia* sp. JB1 | X92188 | CCTTAGTAACGAAGCT | 837-852 | 169 |
| *Denitrobacter permanens* | Y12639 | ACGATGTCAACTAGCT | 789-804 | 170 |
| *Desulfobacter curvatus* | M34413 | CTGCTGTGCCNAAGCT | 861-876 | 171 |
| *Desulfobulbus* sp. BG25 | U85473 | CCTCTGTGTCGCAGCT | 854-869 | 172 |
| *Legionella anisa* | X73394 | ACGATGTCAACTAGCT | 790-805 | 173 |
| Benzene mineralizing clone SB-1 | AF029039 | ATGGTTGTCGTCAGCT | 1029-1044 | 174 |
| *Escherichia coli* | E05133 | CGTGGCTTCCGGAGCT | 848-863 | 175 |
| Uncultured *Acidobacterium* Sub.Div-1 | X68464 | CCGCCGTGCCGAAGCT | 813-828 | 176 |
| Uncultured *Acidobacterium* Sub.Div-1 | Z73363 | CGGCTGTGCCGAAGCT | 521-536 | 177 |
| Uncultured *Acidobacterium* Sub.Div-1 | Z73365 | CCACTGTGCCGTAGCT | 521-536 | 178 |
| Uncultured *Acidobacterium* Sub.Div-1 | Z73368 | CTGCTGTGCCGCAGCT | 521-536 | 179 |
| Uncultured *Acidobacterium* Sub.Div-1 | Z73364 | CTGCCGTGCCGGAGCT | 521-536 | 180 |
| Uncultured *Acidobacterium* Sub.Div-1 | U68659 | CCAATGTGCCGGAGCT | 319-334 | 181 |
| Uncultured *Acidobacterium* Sub.Div-1 | D26171 | CCGTCGTGCCGTAGCT | 79-794 | 182 |
| Uncultured *Acidobacterium* Sub.Div-1 | X97101 | CCGTCGTGTCGTAGCT | 687-702 | 183 |
| Uncultured *Acidobacterium* Sub.Div-1 | X97098 | CTGCCGTGTCGAAGCT | 798-813 | 184 |
| Uncultured *Acidobacterium* Sub.Div-1 | AF047646 | CTCCCGTGTCGAAGCT | 779-794 | 185 |
| Uncultured *Acidobacterium* Sub.Div-1 | AF050548 | CCGCCGTGCCGGAGCT | 316-331 | 186 |
| Uncultured *Acidobacterium* Sub.Div-2 | U68612 | CTGAGGAACGAAAGCT | 226-241 | 187 |
| Uncultured *Acidobacterium* Sub.Div-2 | Y07646 | GTGTCGTCCCGGAGCT | 830-845 | 188 |
| Uncultured *Acidobacterium* Sub.Div-3 | X97097 | GGGCTGTGCCGAAGCT | 804-819 | 189 |
| Uncultured *Acidobacterium* Sub.Div-3 | X68466 | GGTCGGTGCCGGAGCT | 796-811 | 190 |
| Uncultured *Acidobacterium* Sub.Div-3 | X68468 | GGTCGGTGCCAGAGCT | 796-811 | 191 |
| Uncultured *Acidobacterium* Sub.Div-3 | U68648 | GGTTCGTGCCGGAGCT | 317-332 | 192 |
| Uncultured *Acidobacterium* Sub.Div-3 | X68467 | TGTCTGTGCCGGAGCT | 796-811 | 193 |
| Uncultured *Acidobacterium* Sub.Div-3 | AF013515 | TATCCGTGCCGGAGCT | 799-814 | 194 |
| Uncultured *Acidobacterium* Sub.Div-3 | AF027004 | GGTCCGTGCCGGAGCT | 778-793 | 195 |

*Sequences shown in bold with shadow indicates they are not unique to this set.

TABLE II

| Species | GenBank Acc# | Tag Sequence | Position | SEQ ID NO: |
|---|---|---|---|---|
| Crenarchaeota | | | | |
| Aeropyrum pernix | D83259 | CTAGGGGGCGGGAG | 614-627 | 196 |
| Desulfurococcus mobilis | M36474 | CTAGGTGTTGGGTG | 856-869 | 197 |
| Staphylothermus marinus | X99560 | CTAGGTGTTGGGCG | 770-783 | 198 |
| Metallosphaera sedula | X90481 | CTAGGTGTCGCGTA | 756-769 | 199 |
| Sulfolobus acidocaldarius | D14053 | CTAGGTGTCGAGTA | 785-798 | 200 |
| Sulfolobus metallicus | D85519 | CTAGGTGTCACGTG | 744-757 | 201 |
| Caldivirga maquilingensis | AB013926 | CTAGCTGTTGGGTG | 773-786 | 202 |
| Pyrobaculum islandicum | L07511 | CTAGCTGTCGGCCG | 781-794 | 203 |
| Euryarchaeota | | | | |
| Archaeoglobus fulgidus | X05567 | CTAGGTGTCACCGA | 780-793 | 204 |
| Archaeoglobus veneficus | Y10011 | CTAGGTGTCACCGG | 758-771 | 205 |
| Haloarcula japonica | D28872 | CTAGGTGTGGCGTA | 762-775 | 206 |
| Halococcus morrhuae | D11106 | CTAGGTGTGGCGTT | 765-778 | 207 |
| Methanococcus jannaschii | M59126 | CTAGGTGTCGCGTC | 768-781 | 208 |
| Methanobacterium bryantii | AF028688 | None | | |
| Methanobacterium subterraneum | X99045 | None | | |
| Pyrococcus abyssi | Z70246 | CTAGGTGTCGGGCG | 767-780 | 209 |
| Picrophilus oshimae | X84901 | CTAGCTGTAAACTC | 742-755 | 210 |

TABLE III

| Species | GenBank Acc# | Peptide Sequence | M.W. | Position | SEQ ID NO: |
|---|---|---|---|---|---|
| Desulfurobacterium thermolithotrophum | AJ001049 | RAQPLSLVASG* | 1097.40 | 1079-1136 | 211 |
| Uncultured Aquificales OPS132 | AF027104 | RAQPLSCVTSG* | 1117.40 | 1074-1131 | 212 |
| Bacteroides caccae | X83951 | RAQPLSSVTNRSC* | 1417.70 | 1069-1126 | 213 |
| Actinomyces bovis | X81061 | RAQPLSRVASTLWWGLAGD | 2083.60 | 1088-1145 | 214 |
| Actinomyces meyeri | X82451 | RAQPLPYVASTLWWGLVGD | 2128.60 | 1082-1139 | 215 |
| Denitrobacterium detoxificans | AF079507 | RAQPLPHVASIRLGTHGG | 1866.50 | 1039-1094 | 216 |
| Uncultured GNS bacteria BPC110 | AF154084 | RAQPLLYVIRVIPD | 1652.10 | 1074-1116 | 217 |
| Uncultured GNS bacteria GCA004 | AF154104 | RAQPSLYVTRIIRD | 1687.10 | 1080-1122 | 218 |
| Uncultured GNS bacteria GCA112 | AF154100 | RAQPSPYVIRVIRD | 1669.00 | 1082-1124 | 219 |
| Acetobacter aceti | AF127399 | RAQPLSLVASMFGWAL* | 1746.30 | 1038-1095 | 220 |
| Gluconobacter asaii | AB024492 | RAQPLSLVASTFRWAL* | 1815.30 | 1034-1092 | 221 |
| Burkholderia sp.JB1 | X92188 | RAQPLSLVATQEHSRET | 1922.20 | 1094-1144 | 222 |
| Denitrobacter permanens | Y12639 | RAQPLPLVATFSWAL* | 1669.10 | 1077-1131 | 223 |
| Desulfobacter curvatus | M34413 | RAQPLSLVASTLCGNSNET | 1960.40 | 1116-1172 | 224 |
| Desulfobulbus sp.BG25 | U85473 | RAQPLPLVASSSAGHSKGT | 1863.40 | 1114-1170 | 225 |
| Legionella anisa | X73394 | RAQPLSLVAST* | 1141.40 | 1078-1135 | 226 |
| Benzene mineralizing clone SB-1 | AF029039 | RAQPLPLVANRSSWGL* | 1764.20 | 1077-1134 | 227 |
| Escherichia coli | E05133 | RAQPLSFVASGPAGNSKET | 1916.30 | 1103-1159 | 228 |
| Uncultured Acidobacterium Sub.Div-1 | Z73363 | RAQPLSLVASGSSRAL* | 1612.10 | 775-832 | 229 |
| Uncultured Acidobacterium Sub.Div-1 | Z73365 | RAQPLSSVAIGSSRATLAK | 1912.50 | 777-835 | 230 |
| Uncultured Acidobacterium Sub.Div-1 | Z73368 | RAQPLFASCHH* | 1933.50 | 779-835 | 231 |
| Uncultured Acidobacterium Sub.Div-1 | Z73364 | RAQPLFAQLPSFSWALCRN | 2204.80 | 778-835 | 232 |
| Uncultured Acidobacterium Sub.Div-1 | U68659 | RAQPLLPXAII* | 1218.70 | 573-630 | 233 |
| Uncultured Acidobacterium Sub.Div-1 | D26171 | RAQPLLPVATI* | 1177.50 | 1035-1090 | 234 |
| Uncultured Acidobacterium Sub.Div-1 | X97101 | RAQPLSPVAII* | 1163.50 | 943-998 | 235 |
| Uncultured Acidobacterium Sub.Div-1 | X97098 | RAQPLSSVATI* | 1141.40 | 1054-1109 | 236 |
| Uncultured Acidobacterium Sub.Div-1 | AF047646 | RAQPLFLVATI* | 1227.60 | 1035-1090 | 237 |
| Uncultured Acidobacterium Sub.Div-1 | AF050548 | RAQPSSLVANTLW* | 1441.70 | 572-629 | 238 |
| Uncultured Acidobacterium Sub.Div-2 | U68612 | RAQPLHVVATRKRELYVD | 2150.60 | 577-630 | 239 |
| Uncultured Acidobacterium Sub.Div-2 | Y07646 | RAQPLHVVATPQGGTLRG | 1857.30 | 1085-1140 | 240 |
| Uncultured Acidobacterium Sub.Div-3 | X97097 | RAQPSSLVANPQGKHPKGT | 1972.40 | 1060-1116 | 241 |
| Uncultured Acidobacterium Sub.Div-3 | U68648 | RARPLSCVAII* | 1197.70 | 574-629 | 242 |
| Uncultured Acidobacterium Sub.Div-3 | AF013515 | RAQPLSCVANPQGCTLRR | 1969.50 | 1057-1112 | 243 |
| Uncultured Acidobacterium Sub.Div-3 | AF027004 | RAQPSPCVATPPRAGALSGD | 1950.40 | 1036-1096 | 244 |

*Indicates an in-frame stop codon was encountered within the polymorphic sequence.

I claim:

1. A culture-independent method of determining the abundance of an environmental parameter in an environmental sample, said parameter not including bacteria, comprising the steps of:
   a. providing a first plurality of environmental samples at least some of which samples contain the environmental parameter;
   b. isolating a plurality of genomic DNAs from each of the samples provided in step a;
   c. isolating a plurality of 16S rRNA gene segments from each plurality of genomic DNAs isolated in step b;
   d. determining the abundance of each of said 16S rRNA gene segments in each plurality of 16S rRNA gene segments isolated in step c;
   e. determining the abundance of the environmental parameter in each of the samples provided in step a;
   f. correlating the abundance of each 16S rRNA gene segment determined in step d with the abundance of the environmental parameter determined in step e;
   g. selecting at least one 16S rRNA gene segment whose abundance correlates to the abundance of said environmental parameter, as determined in step f;
   h. providing an environmental sample set of at least one environmental sample;
   i. isolating a plurality of genomic DNAs from each environmental sample of the environmental sample set provided in step h;
   j. determining the abundance of said 16S rRNA gene segment selected in step g in each plurality of genomic DNAs isolated in step i; and
   k. inferring the abundance of the environmental parameter in each environmental sample of the environmental sample set provided in step h based upon the abundance of said 16S rRNA gene determined in step j in each environmental sample of the environmental sample set provided in step h.

2. The method according to claim 1, wherein the correlation in step g is expressed by an r-value of 1.

3. The method according to claim 1, wherein the correlation in step g is expressed by an r-value of 0.8 to 0.99.

4. The method according to claim 1, wherein the correlation in step g is expressed by an r-value of 0.5 to 0.7.

5. The method according to claim 1, wherein the environmental parameter is subsurface oil or natural gas.

6. The method of claim 1, wherein the determination in step j, of the abundance of said 16S rRNA gene segment, is done using PCR.

7. The method of claim 1, wherein the determination in step j, of the abundance of said 16S rRNA gene segment, is done using a hybridization assay.

8. A culture-independent method of identifying an indicator for an environmental parameter, said parameter not including bacteria, said method comprising the steps of:
   a. providing a plurality of environmental samples at least some of which samples contain the environmental parameter;
   b. isolating a plurality of genomic DNAs from each of the samples provided in step a;
   c. isolating a plurality of 16S rRNA gene segments from each plurality of genomic DNAs isolated in step b;
   d. determining the abundance of each of said 16S rRNA gene segments in each plurality of 16S rRNA gene segments isolated in step c;
   e. determining the abundance of the environmental parameter in each of the samples provided in step a;
   f. correlating the abundance of each 16S rRNA gene segment determined in step d with the abundance of the environmental parameter determined in step e;
   g. selecting at least one 16S rRNA gene segment whose abundance correlates to the abundance of said environmental parameter, as determined in step f;
   h. designating said 16S rRNA gene segment as the indicator.

9. The method according to claim 8, wherein the correlation in step g is expressed by an r-value of 1.

10. The method according to claim 8, wherein the correlation in step g is expressed by an r-value of 0.8 to 0.99.

11. The method according to claim 8, wherein the correlation in step g is expressed by an r-value of 0.5 to 0.7.

12. The method according to claim 8, wherein the environmental parameter is subsurface oil or natural gas.

13. A culture-independent method of determining the abundance of an environmental parameter in an environmental sample, said parameter not including bacteria, comprising the steps of:
   a. providing at least one environmental sample;
   b. isolating a plurality of genomic DNAs from said environmental sample(s);
   c. determining the abundance of the indicator identified in the method of claim 8 in the plurality of genomic DNAs isolated in step b; and
   d. inferring the abundance of the environmental parameter in said sample(s) based upon the abundance of said indicator in said sample(s).

14. The method according to claim 13, wherein the environmental parameter is subsurface oil or natural gas.

15. The method of claim 13, wherein the abundance of said indicator in said plurality of genomic DNAs is determined using PCR.

16. The method of claim 13, wherein the abundance of said indicator in said plurality of genomic DNAs is determined using a hybridization assay.

17. The method according to claim 1, 8 or 13, wherein the environmental parameter is a mineral deposit.

\* \* \* \* \*

SEQUENCE LISTING

<160> NUMBER OF SEQ ID NOS: 244

<210> SEQ ID NO 1
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 1
acgatgagca ctagct                                                  16

<210> SEQ ID NO 2
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 2
acgatgagta ctagct                                                  16

<210> SEQ ID NO 3
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 3
acgatgatga ctagct                                                  16

<210> SEQ ID NO 4
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 4
acgatggatg ctagct                                                  16

<210> SEQ ID NO 5
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 5
atgctagtct ggagct                                                  16

<210> SEQ ID NO 6
<211> LENGTH: 16
<212> TYPE: DNA
<213> ORGANISM: Unknown
<220> FEATURE:

```
<223> OTHER INFORMATION: ribosomal DNA sequence tag isolated from
      microbes in soil sample collected
      in Wyoming, USA

<400> SEQUENCE: 6
atggctgtcg tcagct                                                      16

<210> SEQ ID NO 7
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 7
atggttgtcg tcagct                                                      16

<210> SEQ ID NO 8
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 8
attccgtgcc gtagct                                                      16

<210> SEQ ID NO 9
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 9
cactagtggc gcagct                                                      16

<210> SEQ ID NO 10
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 10
cccccgtgcc gaagct                                                      16

<210> SEQ ID NO 11
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 11
cccccgtgcc gcagct                                                      16

<210> SEQ ID NO 12
```

```
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 12
cccccttcct ccagct                                                    16

<210> SEQ ID NO 13
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 13
ccccggtgcc gcagct                                                    16

<210> SEQ ID NO 14
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 14
ccgggtagtc ccagct                                                    16

<210> SEQ ID NO 15
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 15
cctccgtgcc gaagct                                                    16

<210> SEQ ID NO 16
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 16
cctccgtgcc gcagct                                                    16

<210> SEQ ID NO 17
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 17
```

```
cctccgtgct gcagct                                                          16
```

<210> SEQ ID NO 18
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 18

```
cctcggcgcc gcagct                                                          16
```

<210> SEQ ID NO 19
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 19

```
cctcggtgcc gcagct                                                          16
```

<210> SEQ ID NO 20
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 20

```
cctcggtgtc gcagct                                                          16
```

<210> SEQ ID NO 21
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 21

```
cctgggtgcc gcagct                                                          16
```

<210> SEQ ID NO 22
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 22

```
cctgtgtgac gaagct                                                          16
```

<210> SEQ ID NO 23
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected in Wyoming, USA

<400> SEQUENCE: 23
ccttggtaac gaagct				16

<210> SEQ ID NO 24
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 24
ccttggtacc gaagct				16

<210> SEQ ID NO 25
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 25
cgccagtgcc gtagct				16

<210> SEQ ID NO 26
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 26
cgcctgtgcc gtagct				16

<210> SEQ ID NO 27
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 27
cgtccgtgcc gaagct				16

<210> SEQ ID NO 28
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 28
cgtccgtgcc gcagct				16

<210> SEQ ID NO 29
<211> LENGTH: 16
<212> TYPE: DNA

```
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 29
cgtcggtgcc gcagct                                                       16

<210> SEQ ID NO 30
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 30
ctcccgtgcc gcagct                                                       16

<210> SEQ ID NO 31
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 31
ctcccgtgcc ggagct                                                       16

<210> SEQ ID NO 32
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 32
ctccggtgcc gcagct                                                       16

<210> SEQ ID NO 33
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 33
ctcctgtgcc gaagct                                                       16

<210> SEQ ID NO 34
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 34
ctcctgtgcc gcagct                                                       16
```

```
<210> SEQ ID NO 35
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 35
ctgccgtgcc gaagct                                                     16

<210> SEQ ID NO 36
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 36
ctgctgtgcc gaagct                                                     16

<210> SEQ ID NO 37
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 37
ctgtcgtgcc gaagct                                                     16

<210> SEQ ID NO 38
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 38
cttcagtatc gaagct                                                     16

<210> SEQ ID NO 39
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 39
cttccgcgcc ggagct                                                     16

<210> SEQ ID NO 40
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA
```

```
<400> SEQUENCE: 40
cttccgtgcc gcagct                                                        16

<210> SEQ ID NO 41
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 41
cttccgtgcc ggagct                                                        16

<210> SEQ ID NO 42
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 42
cttcggtgcc gcagct                                                        16

<210> SEQ ID NO 43
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 43
cttctgtggc gaagct                                                        16

<210> SEQ ID NO 44
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 44
gatccgtgcc gtagct                                                        16

<210> SEQ ID NO 45
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 45
gctctgtgcc gaagct                                                        16

<210> SEQ ID NO 46
<211> LENGTH: 16
<212> TYPE: DNA
<213> ORGANISM: Unknown
<220> FEATURE:
```

-continued

<223> OTHER INFORMATION: ribosomal DNA sequence tag isolated from
      microbes in soil sample collected
      in Wyoming, USA

<400> SEQUENCE: 46
gctgggtgcc caagct                                                      16

<210> SEQ ID NO 47
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 47
ggtccgtgcc gcagct                                                      16

<210> SEQ ID NO 48
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 48
ggtgctcttc ggagct                                                      16

<210> SEQ ID NO 49
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 49
gtaaacgatg gaagct                                                      16

<210> SEQ ID NO 50
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 50
gtggctgtcg tcagct                                                      16

<210> SEQ ID NO 51
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 51
gttccgtgcc gaagct                                                      16

<210> SEQ ID NO 52

```
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 52
gttccgtgcc gcagct                                                        16

<210> SEQ ID NO 53
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 53
tatcagtggc gcagct                                                        16

<210> SEQ ID NO 54
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 54
tctccgtgcc gcagct                                                        16

<210> SEQ ID NO 55
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 55
tctctgtgcc gcagct                                                        16

<210> SEQ ID NO 56
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 56
tctctgtgcc gtagct                                                        16

<210> SEQ ID NO 57
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 57
```

```
tgtccgtgcc gtagct                                                   16

<210> SEQ ID NO 58
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 58
tttccgtgcc gcagct                                                   16

<210> SEQ ID NO 59
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 59
acgatgataa ctagct                                                   16

<210> SEQ ID NO 60
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 60
acgatgatga ctagct                                                   16

<210> SEQ ID NO 61
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 61
acgatgggca ctagct                                                   16

<210> SEQ ID NO 62
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 62
acggctgtcg tcagct                                                   16

<210> SEQ ID NO 63
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
``` in Wyoming, USA

<400> SEQUENCE: 63
actacgagcg caagct                                                          16

<210> SEQ ID NO 64
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 64
acttaatgcg ttagct                                                          16

<210> SEQ ID NO 65
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 65
atgctagtct ggagct                                                          16

<210> SEQ ID NO 66
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 66
atggctctcg tcagct                                                          16

<210> SEQ ID NO 67
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 67
atggctgtcg ccagct                                                          16

<210> SEQ ID NO 68
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 68
atggctgtcg tcagct                                                          16

<210> SEQ ID NO 69
<211> LENGTH: 16
<212> TYPE: DNA

<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 69
atggttgtcg tcagct                                                        16

<210> SEQ ID NO 70
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 70
atgtagacct ggagct                                                        16

<210> SEQ ID NO 71
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 71
attccgtgcc gcagct                                                        16

<210> SEQ ID NO 72
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 72
attccgtgcc gtagct                                                        16

<210> SEQ ID NO 73
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 73
cacaagcggt ggagct                                                        16

<210> SEQ ID NO 74
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 74
cactagtggc gcagct                                                        16

```
<210> SEQ ID NO 75
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 75
catccgtgcc gaagct                                                         16

<210> SEQ ID NO 76
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 76
ccccagggcc caagct                                                         16

<210> SEQ ID NO 77
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 77
ccccggtgcc gcagct                                                         16

<210> SEQ ID NO 78
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 78
cccgcgtgcc ggagct                                                         16

<210> SEQ ID NO 79
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 79
ccgcggtgcc gtagct                                                         16

<210> SEQ ID NO 80
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA
```

```
<400> SEQUENCE: 80
ccgggtagtc ccagct                                                    16

<210> SEQ ID NO 81
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 81
ccgggtagtc ctagct                                                    16

<210> SEQ ID NO 82
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 82
cctccgtgcc gaagct                                                    16

<210> SEQ ID NO 83
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 83
cctccgtgcc gcagct                                                    16

<210> SEQ ID NO 84
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 84
cctccgtgcc ggagct                                                    16

<210> SEQ ID NO 85
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 85
cctcgtaagg ggagct                                                    16

<210> SEQ ID NO 86
<211> LENGTH: 16
<212> TYPE: DNA
<213> ORGANISM: Unknown
<220> FEATURE:
```

<223> OTHER INFORMATION: ribosomal DNA sequence tag isolated from
      microbes in soil sample collected
      in Wyoming, USA

<400> SEQUENCE: 86
cctgggtgcc gcagct                                                   16

<210> SEQ ID NO 87
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 87
cctggtagtc ccagct                                                   16

<210> SEQ ID NO 88
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 88
cctggtagtc ctagct                                                   16

<210> SEQ ID NO 89
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 89
ccttagtaac gcagct                                                   16

<210> SEQ ID NO 90
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 90
ccttggtaac gaagct                                                   16

<210> SEQ ID NO 91
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 91
cgccagtgcc gaagct                                                   16

<210> SEQ ID NO 92

```
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 92
cgccggtgcc gcagct                                                         16

<210> SEQ ID NO 93
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 93
cgcctgtgcc gtagct                                                         16

<210> SEQ ID NO 94
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 94
cgctcgtggc gaagct                                                         16

<210> SEQ ID NO 95
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 95
cggaggcgtc gtagct                                                         16

<210> SEQ ID NO 96
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 96
cgtcagtgtc gcagct                                                         16

<210> SEQ ID NO 97
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 97
```
cgtccgtgcc gaagct					16

<210> SEQ ID NO 98
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 98
cgtccgtgcc gcagct					16

<210> SEQ ID NO 99
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 99
cgtccgtgcc ggagct					16

<210> SEQ ID NO 100
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 100
cgtcggtgcc gcagct					16

<210> SEQ ID NO 101
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 101
ctccagtgcc gcagct					16

<210> SEQ ID NO 102
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 102
ctcccgtgcc acagct					16

<210> SEQ ID NO 103
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected in Wyoming, USA

<400> SEQUENCE: 103
ctcccgtgcc gcagct                                                         16

<210> SEQ ID NO 104
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 104
ctcccgtgcc ggagct                                                         16

<210> SEQ ID NO 105
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 105
ctccggtgcc gcagct                                                         16

<210> SEQ ID NO 106
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 106
ctcctgtgcc gcagct                                                         16

<210> SEQ ID NO 107
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 107
ctgccgcgcc ggagct                                                         16

<210> SEQ ID NO 108
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 108
ctgccgtgcc gaagct                                                         16

<210> SEQ ID NO 109
<211> LENGTH: 16
<212> TYPE: DNA

```
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 109
ctgccgtgcc taagct                                                   16

<210> SEQ ID NO 110
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 110
ctgcggtgcc gcagct                                                   16

<210> SEQ ID NO 111
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 111
ctgctgtgcc gaagct                                                   16

<210> SEQ ID NO 112
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 112
ctgtcgtgcc gaagct                                                   16

<210> SEQ ID NO 113
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 113
cttccgcgcc ggagct                                                   16

<210> SEQ ID NO 114
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 114
cttccgtgcc gaagct                                                   16
```

```
<210> SEQ ID NO 115
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 115
cttccgtgcc gcagct                                                 16

<210> SEQ ID NO 116
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 116
cttccgtgcc ggagct                                                 16

<210> SEQ ID NO 117
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 117
cttcggtgcc gcagct                                                 16

<210> SEQ ID NO 118
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 118
cttcggtgtc gcagct                                                 16

<210> SEQ ID NO 119
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 119
cttgggtgcc gcagct                                                 16

<210> SEQ ID NO 120
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA
```

```
<400> SEQUENCE: 120
ctttagtaac gcagct                                                       16

<210> SEQ ID NO 121
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 121
gacccgcaag ggagct                                                       16

<210> SEQ ID NO 122
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 122
gatccgtgcc gcagct                                                       16

<210> SEQ ID NO 123
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 123
gctccgtgcc gaagct                                                       16

<210> SEQ ID NO 124
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 124
gctccgtgcc gtagct                                                       16

<210> SEQ ID NO 125
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 125
gctctgtgcc gaagct                                                       16

<210> SEQ ID NO 126
<211> LENGTH: 16
<212> TYPE: DNA
<213> ORGANISM: Unknown
<220> FEATURE:
```

```
<223> OTHER INFORMATION: ribosomal DNA sequence tag isolated from
      microbes in soil sample collected
      in Wyoming, USA

<400> SEQUENCE: 126
gctctgtgcc gtagct                                                 16

<210> SEQ ID NO 127
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 127
gggcttgtcg tcagct                                                 16

<210> SEQ ID NO 128
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 128
gtaaacgatg gaagct                                                 16

<210> SEQ ID NO 129
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 129
gttccgtgcc gcagct                                                 16

<210> SEQ ID NO 130
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 130
gttccgtgcc gtagct                                                 16

<210> SEQ ID NO 131
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 131
gttctgtgcc gcagct                                                 16

<210> SEQ ID NO 132
```

```
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 132
tctcacgaca cgagct                                                16

<210> SEQ ID NO 133
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 133
tctcagtaac gtagct                                                16

<210> SEQ ID NO 134
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 134
tctccgtgcc gcagct                                                16

<210> SEQ ID NO 135
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 135
tctctgtgcc gcagct                                                16

<210> SEQ ID NO 136
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 136
tggacgttgc ggagct                                                16

<210> SEQ ID NO 137
<211> LENGTH: 16
<212> TYPE: DNA
<213> ORGANISM: Unknown
<220> FEATURE:
<223> OTHER INFORMATION: ribosomal DNA sequence tag isolated from
      microbes in soil sample collected
      in Wyoming, USA

<400> SEQUENCE: 137
```
tttccgtgcc ggagct                                                    16

<210> SEQ ID NO 138
<211> LENGTH: 20
<212> TYPE: DNA
<213> ORGANISM: Artificial Sequence
<220> FEATURE:
<223> OTHER INFORMATION: Oligonucleotide
<220> FEATURE:
<221> NAME/KEY: modified_base
<222> LOCATION: (1)..(1)
<223> OTHER INFORMATION: Biotin

<400> SEQUENCE: 138
gtgtaghrgt gaaatdcdya                                                20

<210> SEQ ID NO 139
<211> LENGTH: 21
<212> TYPE: DNA
<213> ORGANISM: Artificial Sequence
<220> FEATURE:
<223> OTHER INFORMATION: Oligonucleotide

<400> SEQUENCE: 139
ytcacgrcay gagctgacga c                                              21

<210> SEQ ID NO 140
<211> LENGTH: 28
<212> TYPE: DNA
<213> ORGANISM: Artificial Sequence
<220> FEATURE:
<223> OTHER INFORMATION: Oligonucleotide
<220> FEATURE:
<221> NAME/KEY: modified_base
<222> LOCATION: (1)..(1)
<223> OTHER INFORMATION: 5' Phosphate
<220> FEATURE:
<221> NAME/KEY: modified_base
<222> LOCATION: (28)..(28)
<223> OTHER INFORMATION: Dideoxy

<400> SEQUENCE: 140
gctccaggtc tacatcctag tcaggacc                                       28

<210> SEQ ID NO 141
<211> LENGTH: 24
<212> TYPE: DNA
<213> ORGANISM: Artificial Sequence
<220> FEATURE:
<223> OTHER INFORMATION: Oligonucleotide

<400> SEQUENCE: 141
ataggtcctg actaggatgt agac                                           24

<210> SEQ ID NO 142
<211> LENGTH: 28
<212> TYPE: DNA
<213> ORGANISM: Artificial Sequence
<220> FEATURE:
<223> OTHER INFORMATION: Oligonucleotide
<220> FEATURE:
<221> NAME/KEY: modified_base
<222> LOCATION: (1)..(1)
<223> OTHER INFORMATION: 5' Phosphate
<220> FEATURE:
<221> NAME/KEY: modified_base
<222> LOCATION: (28)..(28)
<223> OTHER INFORMATION: Dideoxy

<400> SEQUENCE: 142

```
gctccagact agcatccgct gacttgac                                          28

<210> SEQ ID NO 143
<211> LENGTH: 24
<212> TYPE: DNA
<213> ORGANISM: Artificial Sequence
<220> FEATURE:
<223> OTHER INFORMATION: Oligonucleotide

<400> SEQUENCE: 143
aatgtcaagt cagcggatgc tagt                                              24

<210> SEQ ID NO 144
<211> LENGTH: 21
<212> TYPE: DNA
<213> ORGANISM: Artificial Sequence
<220> FEATURE:
<223> OTHER INFORMATION: Oligonucleotide
<220> FEATURE:
<221> NAME/KEY: modified_base
<222> LOCATION: (1)..(1)
<223> OTHER INFORMATION: Biotin

<400> SEQUENCE: 144
ggtcctgact aggatgtaga c                                                 21

<210> SEQ ID NO 145
<211> LENGTH: 21
<212> TYPE: DNA
<213> ORGANISM: Artificial Sequence
<220> FEATURE:
<223> OTHER INFORMATION: Oligonucleotide
<220> FEATURE:
<221> NAME/KEY: modified_base
<222> LOCATION: (1)..(1)
<223> OTHER INFORMATION: Biotin

<400> SEQUENCE: 145
gtcaagtcag cggatgctag t                                                 21

<210> SEQ ID NO 146
<211> LENGTH: 21
<212> TYPE: DNA
<213> ORGANISM: Artificial Sequence
<220> FEATURE:
<223> OTHER INFORMATION: Oligonucleotide
<220> FEATURE:
<221> NAME/KEY: modified_base
<222> LOCATION: (1)..(1)
<223> OTHER INFORMATION: Biotin

<400> SEQUENCE: 146
ggattagawa cccbggtagt c                                                 21

<210> SEQ ID NO 147
<211> LENGTH: 30
<212> TYPE: DNA
<213> ORGANISM: Artificial Sequence
<220> FEATURE:
<223> OTHER INFORMATION: Oligonucleotide

<400> SEQUENCE: 147
ataggtcctg actaggatgt agacctggag                                        30

<210> SEQ ID NO 148
<211> LENGTH: 30
<212> TYPE: DNA
<213> ORGANISM: Artificial Sequence
<220> FEATURE:
```

<223> OTHER INFORMATION: Oligonucleotide

<400> SEQUENCE: 148
aatgtcaagt cagcggatgc tagtctggag                              30

<210> SEQ ID NO 149
<211> LENGTH: 27
<212> TYPE: DNA
<213> ORGANISM: Artificial Sequence
<220> FEATURE:
<223> OTHER INFORMATION: Oligonucleotide
<220> FEATURE:
<221> NAME/KEY: modified_base
<222> LOCATION: (1)..(1)
<223> OTHER INFORMATION: 5' Phosphate
<220> FEATURE:
<221> NAME/KEY: modified_base
<222> LOCATION: (27)..(27)
<223> OTHER INFORMATION: Dideoxy

<400> SEQUENCE: 149
ctccaggtct acatcctagt caggacc                                 27

<210> SEQ ID NO 150
<211> LENGTH: 30
<212> TYPE: DNA
<213> ORGANISM: Artificial Sequence
<220> FEATURE:
<223> OTHER INFORMATION: Oligonucleotide

<400> SEQUENCE: 150
ataggtcctg actaggatgt agacctggag                              30

<210> SEQ ID NO 151
<211> LENGTH: 27
<212> TYPE: DNA
<213> ORGANISM: Artificial Sequence
<220> FEATURE:
<223> OTHER INFORMATION: Oligonucleotide
<220> FEATURE:
<221> NAME/KEY: modified_base
<222> LOCATION: (1)..(1)
<223> OTHER INFORMATION: 5' Phosphate
<220> FEATURE:
<221> NAME/KEY: modified_base
<222> LOCATION: (27)..(27)
<223> OTHER INFORMATION: Dideoxy

<400> SEQUENCE: 151
ctccagacta gcatccgctg acttgac                                 27

<210> SEQ ID NO 152
<211> LENGTH: 30
<212> TYPE: DNA
<213> ORGANISM: Artificial Sequence
<220> FEATURE:
<223> OTHER INFORMATION: Oligonucleotide

<400> SEQUENCE: 152
aatgtcaagt cagcggatgc tagtctggag                              30

<210> SEQ ID NO 153
<211> LENGTH: 33
<212> TYPE: DNA
<213> ORGANISM: Artificial Sequence
<220> FEATURE:
<223> OTHER INFORMATION: Oligonucleotide
<220> FEATURE:
<221> NAME/KEY: modified_base
<222> LOCATION: (1)..(1)

-continued

```
<223> OTHER INFORMATION: Biotin

<400> SEQUENCE: 153
ctcgatagtc acggtcctga ctaggatgta gac                                    33

<210> SEQ ID NO 154
<211> LENGTH: 33
<212> TYPE: DNA
<213> ORGANISM: Artificial Sequence
<220> FEATURE:
<223> OTHER INFORMATION: Oligonucleotide
<220> FEATURE:
<221> NAME/KEY: modified_base
<222> LOCATION: (1)..(1)
<223> OTHER INFORMATION: Biotin

<400> SEQUENCE: 154
caggttgcaa cggtcaagtc agcggatgct agt                                    33

<210> SEQ ID NO 155
<211> LENGTH: 22
<212> TYPE: DNA
<213> ORGANISM: Artificial Sequence
<220> FEATURE:
<223> OTHER INFORMATION: Oligonucleotide
<220> FEATURE:
<221> NAME/KEY: modified_base
<222> LOCATION: (1)..(1)
<223> OTHER INFORMATION: biotin
<220> FEATURE:
<221> NAME/KEY: misc_feature
<222> LOCATION: (22)..(22)
<223> OTHER INFORMATION: A, G, C or T

<400> SEQUENCE: 155
taytycccar gcggybsrct tn                                                22

<210> SEQ ID NO 156
<211> LENGTH: 25
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (25)..(25)
<223> OTHER INFORMATION: A, G, C or T

<400> SEQUENCE: 156
ggtgbcascm gccgcggtaa yaccn                                             25

<210> SEQ ID NO 157
<211> LENGTH: 22
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (14)..(22)
<223> OTHER INFORMATION: A, G, C or T

<400> SEQUENCE: 157
aacgagcgca accnnnnnnn nn                                                22

<210> SEQ ID NO 158
<211> LENGTH: 16
<212> TYPE: DNA
<213> ORGANISM: Desulfurobacterium thermolithotrophum
```

```
<400> SEQUENCE: 158
gtcagttgcc gaagct                                                    16

<210> SEQ ID NO 159
<211> LENGTH: 16
<212> TYPE: DNA
<213> ORGANISM: Uncultured Aquificales OPS132

<400> SEQUENCE: 159
gtccgtgccg taagct                                                    16

<210> SEQ ID NO 160
<211> LENGTH: 16
<212> TYPE: DNA
<213> ORGANISM: Bacteroides caccae

<400> SEQUENCE: 160
atggttgtcg tcagct                                                    16

<210> SEQ ID NO 161
<211> LENGTH: 16
<212> TYPE: DNA
<213> ORGANISM: Actinomyces bovis

<400> SEQUENCE: 161
tttccgcgcc gtagct                                                    16

<210> SEQ ID NO 162
<211> LENGTH: 16
<212> TYPE: DNA
<213> ORGANISM: Actinomyces meyeri

<400> SEQUENCE: 162
tttctgcgcc gtagct                                                    16

<210> SEQ ID NO 163
<211> LENGTH: 16
<212> TYPE: DNA
<213> ORGANISM: Denitrobacterium detoxificans

<400> SEQUENCE: 163
cctccgcgcc gcagct                                                    16

<210> SEQ ID NO 164
<211> LENGTH: 16
<212> TYPE: DNA
<213> ORGANISM: Uncultured GNS bacteria BPC110

<400> SEQUENCE: 164
cccggtagtc ctagct                                                    16

<210> SEQ ID NO 165
<211> LENGTH: 16
<212> TYPE: DNA
<213> ORGANISM: Uncultured GNS bacteria GCA004

<400> SEQUENCE: 165
catcggtgcc gcagct                                                    16

<210> SEQ ID NO 166
<211> LENGTH: 16
<212> TYPE: DNA
<213> ORGANISM: Uncultured GNS bacteria GCA112
```

-continued

```
<400> SEQUENCE: 166
cggcggtgcc gtagct                                                    16

<210> SEQ ID NO 167
<211> LENGTH: 16
<212> TYPE: DNA
<213> ORGANISM: Acetobacter aceti

<400> SEQUENCE: 167
actcagtgtc gtagct                                                    16

<210> SEQ ID NO 168
<211> LENGTH: 16
<212> TYPE: DNA
<213> ORGANISM: Gluconobacter asaii

<400> SEQUENCE: 168
actcagtgtc gaagct                                                    16

<210> SEQ ID NO 169
<211> LENGTH: 16
<212> TYPE: DNA
<213> ORGANISM: Burkholderia sp. JB1

<400> SEQUENCE: 169
ccttagtaac gaagct                                                    16

<210> SEQ ID NO 170
<211> LENGTH: 16
<212> TYPE: DNA
<213> ORGANISM: Denitrobacter permanens

<400> SEQUENCE: 170
acgatgtcaa ctagct                                                    16

<210> SEQ ID NO 171
<211> LENGTH: 16
<212> TYPE: DNA
<213> ORGANISM: Desulfobacter curvatus
<220> FEATURE:
<221> NAME/KEY: misc_feature
<222> LOCATION: (11)..(11)
<223> OTHER INFORMATION: A, G, C or T

<400> SEQUENCE: 171
ctgctgtgcc naagct                                                    16

<210> SEQ ID NO 172
<211> LENGTH: 16
<212> TYPE: DNA
<213> ORGANISM: Desulfobulbus sp. BG25

<400> SEQUENCE: 172
cctctgtgtc gcagct                                                    16

<210> SEQ ID NO 173
<211> LENGTH: 16
<212> TYPE: DNA
<213> ORGANISM: Legionella anisa

<400> SEQUENCE: 173
acgatgtcaa ctagct                                                    16

<210> SEQ ID NO 174
```

```
<211> LENGTH: 16
<212> TYPE: DNA
<213> ORGANISM: Benzene mineralizing clone SB-1

<400> SEQUENCE: 174
atggttgtcg tcagct                                                        16

<210> SEQ ID NO 175
<211> LENGTH: 16
<212> TYPE: DNA
<213> ORGANISM: Escherichia coli

<400> SEQUENCE: 175
cgtggcttcc ggagct                                                        16

<210> SEQ ID NO 176
<211> LENGTH: 16
<212> TYPE: DNA
<213> ORGANISM: Uncultured Acidobacterium Sub.Div-1

<400> SEQUENCE: 176
ccgccgtgcc gaagct                                                        16

<210> SEQ ID NO 177
<211> LENGTH: 16
<212> TYPE: DNA
<213> ORGANISM: Uncultured Acidobacterium Sub.Div-1

<400> SEQUENCE: 177
cggctgtgcc gaagct                                                        16

<210> SEQ ID NO 178
<211> LENGTH: 16
<212> TYPE: DNA
<213> ORGANISM: Uncultured Acidobacterium Sub.Div-1

<400> SEQUENCE: 178
ccactgtgcc gtagct                                                        16

<210> SEQ ID NO 179
<211> LENGTH: 16
<212> TYPE: DNA
<213> ORGANISM: Uncultured Acidobacterium Sub.Div-1

<400> SEQUENCE: 179
ctgctgtgcc gcagct                                                        16

<210> SEQ ID NO 180
<211> LENGTH: 16
<212> TYPE: DNA
<213> ORGANISM: Uncultured Acidobacterium Sub.Div-1

<400> SEQUENCE: 180
ctgccgtgcc ggagct                                                        16

<210> SEQ ID NO 181
<211> LENGTH: 16
<212> TYPE: DNA
<213> ORGANISM: Uncultured Acidobacterium Sub.Div-1

<400> SEQUENCE: 181
ccaatgtgcc ggagct                                                        16

<210> SEQ ID NO 182
```

```
<211> LENGTH: 16
<212> TYPE: DNA
<213> ORGANISM: Uncultured Acidobacterium Sub.Div-1

<400> SEQUENCE: 182
ccgtcgtgcc gtagct                                                    16

<210> SEQ ID NO 183
<211> LENGTH: 16
<212> TYPE: DNA
<213> ORGANISM: Uncultured Acidobacterium Sub.Div-1

<400> SEQUENCE: 183
ccgtcgtgtc gtagct                                                    16

<210> SEQ ID NO 184
<211> LENGTH: 16
<212> TYPE: DNA
<213> ORGANISM: Uncultured Acidobacterium Sub.Div-1

<400> SEQUENCE: 184
ctgccgtgtc gaagct                                                    16

<210> SEQ ID NO 185
<211> LENGTH: 16
<212> TYPE: DNA
<213> ORGANISM: Uncultured Acidobacterium Sub.Div-1

<400> SEQUENCE: 185
ctcccgtgtc gaagct                                                    16

<210> SEQ ID NO 186
<211> LENGTH: 16
<212> TYPE: DNA
<213> ORGANISM: Uncultured Acidobacterium Sub.Div-1

<400> SEQUENCE: 186
ccgccgtgcc ggagct                                                    16

<210> SEQ ID NO 187
<211> LENGTH: 16
<212> TYPE: DNA
<213> ORGANISM: Uncultured Acidobacterium Sub.Div-2

<400> SEQUENCE: 187
ctgaggaacg aaagct                                                    16

<210> SEQ ID NO 188
<211> LENGTH: 16
<212> TYPE: DNA
<213> ORGANISM: Uncultured Acidobacterium Sub.Div-2

<400> SEQUENCE: 188
gtgtcgtccc ggagct                                                    16

<210> SEQ ID NO 189
<211> LENGTH: 16
<212> TYPE: DNA
<213> ORGANISM: Uncultured Acidobacterium Sub.Div-3

<400> SEQUENCE: 189
gggctgtgcc gaagct                                                    16

<210> SEQ ID NO 190
```

```
<211> LENGTH: 16
<212> TYPE: DNA
<213> ORGANISM: Uncultured Acidobacterium Sub.Div-3

<400> SEQUENCE: 190
ggtcggtgcc ggagct                                                    16

<210> SEQ ID NO 191
<211> LENGTH: 16
<212> TYPE: DNA
<213> ORGANISM: Uncultured Acidobacterium Sub.Div-3

<400> SEQUENCE: 191
ggtcggtgcc agagct                                                    16

<210> SEQ ID NO 192
<211> LENGTH: 16
<212> TYPE: DNA
<213> ORGANISM: Uncultured Acidobacterium Sub.Div-3

<400> SEQUENCE: 192
ggttcgtgcc ggagct                                                    16

<210> SEQ ID NO 193
<211> LENGTH: 16
<212> TYPE: DNA
<213> ORGANISM: Uncultured Acidobacterium Sub.Div-3

<400> SEQUENCE: 193
tgtctgtgcc ggagct                                                    16

<210> SEQ ID NO 194
<211> LENGTH: 16
<212> TYPE: DNA
<213> ORGANISM: Uncultured Acidobacterium Sub.Div-3

<400> SEQUENCE: 194
tatccgtgcc ggagct                                                    16

<210> SEQ ID NO 195
<211> LENGTH: 16
<212> TYPE: DNA
<213> ORGANISM: Uncultured Acidobacterium Sub.Div-3

<400> SEQUENCE: 195
ggtccgtgcc ggagct                                                    16

<210> SEQ ID NO 196
<211> LENGTH: 14
<212> TYPE: DNA
<213> ORGANISM: Aeropyrum pernix

<400> SEQUENCE: 196 ctaggggcg ggag                                                       14

<210> SEQ ID NO 197
<211> LENGTH: 14
<212> TYPE: DNA
<213> ORGANISM: Desulfurococcus mobilis

<400> SEQUENCE: 197
ctaggtgttg ggtg                                                      14

<210> SEQ ID NO 198
```

```
<211> LENGTH: 14
<212> TYPE: DNA
<213> ORGANISM: Staphylothermus marinus

<400> SEQUENCE: 198
ctaggtgttg ggcg                                                     14

<210> SEQ ID NO 199
<211> LENGTH: 14
<212> TYPE: DNA
<213> ORGANISM: Metallosphaera sedula

<400> SEQUENCE: 199
ctaggtgtcg cgta                                                     14

<210> SEQ ID NO 200
<211> LENGTH: 14
<212> TYPE: DNA
<213> ORGANISM: Sulfolobus acidocaldarius

<400> SEQUENCE: 200
ctaggtgtcg agta                                                     14

<210> SEQ ID NO 201
<211> LENGTH: 14
<212> TYPE: DNA
<213> ORGANISM: Sulfolobus metallicus

<400> SEQUENCE: 201
ctaggtgtca cgtg                                                     14

<210> SEQ ID NO 202
<211> LENGTH: 14
<212> TYPE: DNA
<213> ORGANISM: Caldivirga maquilingensis

<400> SEQUENCE: 202
ctagctgttg ggtg                                                     14

<210> SEQ ID NO 203
<211> LENGTH: 14
<212> TYPE: DNA
<213> ORGANISM: Pyrobaculum islandicum

<400> SEQUENCE: 203
ctagctgtcg gccg                                                     14

<210> SEQ ID NO 204
<211> LENGTH: 14
<212> TYPE: DNA
<213> ORGANISM: Archaeoglobus fulgidus

<400> SEQUENCE: 204
ctaggtgtca ccga                                                     14

<210> SEQ ID NO 205
<211> LENGTH: 14
<212> TYPE: DNA
<213> ORGANISM: Archaeoglobus veneficus

<400> SEQUENCE: 205
ctaggtgtca ccgg                                                     14

<210> SEQ ID NO 206
```

```
<210> SEQ ID NO 206
<211> LENGTH: 14
<212> TYPE: DNA
<213> ORGANISM: Haloarcula japonica

<400> SEQUENCE: 206
ctaggtgtgg cgta                                                     14

<210> SEQ ID NO 207
<211> LENGTH: 14
<212> TYPE: DNA
<213> ORGANISM: Halococcus morrhuae

<400> SEQUENCE: 207
ctaggtgtgg cgtt                                                     14

<210> SEQ ID NO 208
<211> LENGTH: 14
<212> TYPE: DNA
<213> ORGANISM: Methanococcus jannaschii

<400> SEQUENCE: 208
ctaggtgtcg cgtc                                                     14

<210> SEQ ID NO 209
<211> LENGTH: 14
<212> TYPE: DNA
<213> ORGANISM: Pyrococcus abyssi

<400> SEQUENCE: 209
ctaggtgtcg ggcg                                                     14

<210> SEQ ID NO 210
<211> LENGTH: 14
<212> TYPE: DNA
<213> ORGANISM: Picrophilus oshimae

<400> SEQUENCE: 210
ctagctgtaa actc                                                     14

<210> SEQ ID NO 211
<211> LENGTH: 11
<212> TYPE: PRT
<213> ORGANISM: Desulfurobacterium thermolithotrophum

<400> SEQUENCE: 211

Arg Ala Gln Pro Leu Ser Leu Val Ala Ser Gly
1               5                   10

<210> SEQ ID NO 212
<211> LENGTH: 11
<212> TYPE: PRT
<213> ORGANISM: Uncultured Aquificales OPS132

<400> SEQUENCE: 212

Arg Ala Gln Pro Leu Ser Cys Val Thr Ser Gly
1               5                   10

<210> SEQ ID NO 213
<211> LENGTH: 13
<212> TYPE: PRT
<213> ORGANISM: Bacteroides caccae

<400> SEQUENCE: 213

Arg Ala Gln Pro Leu Ser Ser Val Thr Asn Arg Ser Cys
1               5                   10
```

<210> SEQ ID NO 214
<211> LENGTH: 19
<212> TYPE: PRT
<213> ORGANISM: Actinomyces bovis

<400> SEQUENCE: 214

Arg Ala Gln Pro Leu Ser Arg Val Ala Ser Thr Leu Trp Trp Gly Leu
1               5                   10                  15

Ala Gly Asp

<210> SEQ ID NO 215
<211> LENGTH: 19
<212> TYPE: PRT
<213> ORGANISM: Actinomyces meyeri

<400> SEQUENCE: 215

Arg Ala Gln Pro Leu Pro Tyr Val Ala Ser Thr Leu Trp Trp Gly Leu
1               5                   10                  15

Val Gly Asp

<210> SEQ ID NO 216
<211> LENGTH: 18
<212> TYPE: PRT
<213> ORGANISM: Denitrobacterium detoxificans

<400> SEQUENCE: 216

Arg Ala Gln Pro Leu Pro His Val Ala Ser Ile Arg Leu Gly Thr His
1               5                   10                  15

Gly Gly

<210> SEQ ID NO 217
<211> LENGTH: 14
<212> TYPE: PRT
<213> ORGANISM: Uncultured GNS bacteria BPC110

<400> SEQUENCE: 217

Arg Ala Gln Pro Leu Leu Tyr Val Ile Arg Val Ile Pro Asp
1               5                   10

<210> SEQ ID NO 218
<211> LENGTH: 14
<212> TYPE: PRT
<213> ORGANISM: Uncultured GNS bacteria GCA004

<400> SEQUENCE: 218

Arg Ala Gln Pro Ser Leu Tyr Val Thr Arg Ile Ile Arg Asp
1               5                   10

<210> SEQ ID NO 219
<211> LENGTH: 14
<212> TYPE: PRT
<213> ORGANISM: Uncultured GNS bacteria GCA112

<400> SEQUENCE: 219

Arg Ala Gln Pro Ser Pro Tyr Val Ile Arg Val Ile Arg Asp
1               5                   10

<210> SEQ ID NO 220
<211> LENGTH: 16
<212> TYPE: PRT
<213> ORGANISM: Acetobacter aceti

<400> SEQUENCE: 220

Arg Ala Gln Pro Leu Ser Leu Val Ala Ser Met Phe Gly Trp Ala Leu
1               5                   10                  15

<210> SEQ ID NO 221
<211> LENGTH: 16
<212> TYPE: PRT
<213> ORGANISM: Gluconobacter asaii

<400> SEQUENCE: 221

Arg Ala Gln Pro Leu Ser Leu Val Ala Ser Thr Phe Arg Trp Ala Leu
1               5                   10                  15

<210> SEQ ID NO 222
<211> LENGTH: 17
<212> TYPE: PRT
<213> ORGANISM: Burkholderia sp. JB1

<400> SEQUENCE: 222

Arg Ala Gln Pro Leu Ser Leu Val Ala Thr Gln Glu His Ser Arg Glu
1               5                   10                  15

Thr

<210> SEQ ID NO 223
<211> LENGTH: 15
<212> TYPE: PRT
<213> ORGANISM: Denitrobacter permanens

<400> SEQUENCE: 223

Arg Ala Gln Pro Leu Pro Leu Val Ala Thr Phe Ser Trp Ala Leu
1               5                   10                  15

<210> SEQ ID NO 224
<211> LENGTH: 19
<212> TYPE: PRT
<213> ORGANISM: Desulfobacter curvatus

<400> SEQUENCE: 224

Arg Ala Gln Pro Leu Ser Leu Val Ala Ser Thr Leu Cys Gly Asn Ser
1               5                   10                  15

Asn Glu Thr

<210> SEQ ID NO 225
<211> LENGTH: 19
<212> TYPE: PRT
<213> ORGANISM: Desulfobulbus sp. BG25

<400> SEQUENCE: 225

Arg Ala Gln Pro Leu Pro Leu Val Ala Ser Ser Ser Ala Gly His Ser
1               5                   10                  15

Lys Gly Thr

<210> SEQ ID NO 226
<211> LENGTH: 11
<212> TYPE: PRT
<213> ORGANISM: Legionella anisa

<400> SEQUENCE: 226

Arg Ala Gln Pro Leu Ser Leu Val Ala Ser Thr
1               5                   10

<210> SEQ ID NO 227
<211> LENGTH: 16
<212> TYPE: PRT

-continued

<213> ORGANISM: Benzene mineralizing clone SB-1

<400> SEQUENCE: 227

Arg Ala Gln Pro Leu Pro Leu Val Ala Asn Arg Ser Ser Trp Gly Leu
1               5                   10                  15

<210> SEQ ID NO 228
<211> LENGTH: 19
<212> TYPE: PRT
<213> ORGANISM: Escherichia coli

<400> SEQUENCE: 228

Arg Ala Gln Pro Leu Ser Phe Val Ala Ser Gly Pro Ala Gly Asn Ser
1               5                   10                  15

Lys Glu Thr

<210> SEQ ID NO 229
<211> LENGTH: 16
<212> TYPE: PRT
<213> ORGANISM: Uncultured Acidobacterium Sub.Div-1

<400> SEQUENCE: 229

Arg Ala Gln Pro Leu Ser Leu Val Ala Ser Gly Ser Ser Arg Ala Leu
1               5                   10                  15

<210> SEQ ID NO 230
<211> LENGTH: 19
<212> TYPE: PRT
<213> ORGANISM: Uncultured Acidobacterium Sub.Div-1

<400> SEQUENCE: 230

Arg Ala Gln Pro Leu Ser Ser Val Ala Ile Gly Ser Ser Arg Ala Thr
1               5                   10                  15

Leu Ala Lys

<210> SEQ ID NO 231
<211> LENGTH: 11
<212> TYPE: PRT
<213> ORGANISM: Uncultured Acidobacterium Sub.Div-1

<400> SEQUENCE: 231

Arg Ala Gln Pro Leu Phe Ala Ser Cys His His
1               5                   10

<210> SEQ ID NO 232
<211> LENGTH: 19
<212> TYPE: PRT
<213> ORGANISM: Uncultured Acidobacterium Sub.Div-1

<400> SEQUENCE: 232

Arg Ala Gln Pro Leu Phe Ala Gln Leu Pro Ser Phe Ser Trp Ala Leu
1               5                   10                  15

Cys Arg Asn

<210> SEQ ID NO 233
<211> LENGTH: 11
<212> TYPE: PRT
<213> ORGANISM: Uncultured Acidobacterium Sub.Div-1
<220> FEATURE:
<221> NAME/KEY: MISC_FEATURE
<222> LOCATION: (8)..(8)
<223> OTHER INFORMATION: Unable to determine

<400> SEQUENCE: 233

```
Arg Ala Gln Pro Leu Leu Pro Xaa Ala Ile Ile
1               5                   10

<210> SEQ ID NO 234
<211> LENGTH: 11
<212> TYPE: PRT
<213> ORGANISM: Uncultured Acidobacterium Sub.Div-1

<400> SEQUENCE: 234

Arg Ala Gln Pro Leu Leu Pro Val Ala Thr Ile
1               5                   10

<210> SEQ ID NO 235
<211> LENGTH: 11
<212> TYPE: PRT
<213> ORGANISM: Uncultured Acidobacterium Sub.Div-1

<400> SEQUENCE: 235

Arg Ala Gln Pro Leu Ser Pro Val Ala Ile Ile
1               5                   10

<210> SEQ ID NO 236
<211> LENGTH: 11
<212> TYPE: PRT
<213> ORGANISM: Uncultured Acidobacterium Sub.Div-1

<400> SEQUENCE: 236

Arg Ala Gln Pro Leu Ser Ser Val Ala Thr Ile
1               5                   10

<210> SEQ ID NO 237
<211> LENGTH: 11
<212> TYPE: PRT
<213> ORGANISM: Uncultured Acidobacterium Sub.Div-1

<400> SEQUENCE: 237

Arg Ala Gln Pro Leu Phe Leu Val Ala Thr Ile
1               5                   10

<210> SEQ ID NO 238
<211> LENGTH: 13
<212> TYPE: PRT
<213> ORGANISM: Uncultured Acidobacterium Sub.Div-1

<400> SEQUENCE: 238

Arg Ala Gln Pro Ser Ser Leu Val Ala Asn Thr Leu Trp
1               5                   10

<210> SEQ ID NO 239
<211> LENGTH: 18
<212> TYPE: PRT
<213> ORGANISM: Uncultured Acidobacterium Sub.Div-2

<400> SEQUENCE: 239

Arg Ala Gln Pro Leu His Val Val Ala Thr Arg Lys Arg Glu Leu Tyr
1               5                   10                  15

Val Asp

<210> SEQ ID NO 240
<211> LENGTH: 18
<212> TYPE: PRT
<213> ORGANISM: Uncultured Acidobacterium Sub.Div-2

<400> SEQUENCE: 240

Arg Ala Gln Pro Leu His Val Val Ala Thr Pro Gln Gly Gly Thr Leu
```

-continued

```
                1               5              10              15

Arg Gly

<210> SEQ ID NO 241
<211> LENGTH: 19
<212> TYPE: PRT
<213> ORGANISM: Uncultured Acidobacterium Sub.Div-3

<400> SEQUENCE: 241

Arg Ala Gln Pro Ser Ser Leu Val Ala Asn Pro Gln Gly Lys His Pro
1               5                   10                  15

Lys Gly Thr

<210> SEQ ID NO 242
<211> LENGTH: 11
<212> TYPE: PRT
<213> ORGANISM: Uncultured Acidobacterium Sub.Div-3

<400> SEQUENCE: 242

Arg Ala Arg Pro Leu Ser Cys Val Ala Ile Ile
1               5                   10

<210> SEQ ID NO 243
<211> LENGTH: 18
<212> TYPE: PRT
<213> ORGANISM: Uncultured Acidobacterium Sub.Div-3

<400> SEQUENCE: 243

Arg Ala Gln Pro Leu Ser Cys Val Ala Asn Pro Gln Gly Cys Thr Leu
1               5                   10                  15

Arg Arg

<210> SEQ ID NO 244
<211> LENGTH: 20
<212> TYPE: PRT
<213> ORGANISM: Uncultured Acidobacterium Sub.Div-3

<400> SEQUENCE: 244

Arg Ala Gln Pro Ser Pro Cys Val Ala Thr Pro Pro Arg Ala Gly Ala
1               5                   10                  15

Leu Ser Gly Asp
                20
```